United States Patent [19]

Meyer, Jr. et al.

[11] Patent Number: 5,574,142
[45] Date of Patent: Nov. 12, 1996

[54] PEPTIDE LINKERS FOR IMPROVED OLIGONUCLEOTIDE DELIVERY

[75] Inventors: Rich B. Meyer, Jr., Woodinville; Alexander A. Gall, Bothell; Michael W. Reed, Seattle, all of Wash.

[73] Assignee: MicroProbe Corporation, Bothell, Wash.

[21] Appl. No.: 991,199

[22] Filed: Dec. 15, 1992

[51] Int. Cl.$^6$ .............................. C07H 21/04; C07K 4/00
[52] U.S. Cl. ...................... 536/23.1; 536/24.1; 536/25.6; 530/300
[58] Field of Search ................................ 536/23.1, 24.1, 536/25.6; 530/300

[56] References Cited

FOREIGN PATENT DOCUMENTS

| | | | |
|---|---|---|---|
| 0044090 | 1/1982 | European Pat. Off. | C07C 103/52 |
| 0055991 | 7/1982 | European Pat. Off. | A61K 31/395 |
| WO93/04701 | 3/1993 | WIPO | A61K 48/00 |
| WO93/23570 | 11/1993 | WIPO | C12Q 1/68 |

OTHER PUBLICATIONS

Duncan (1992) Anti–Cancer Drugs 3, 175–210.
Milligan et al. (1993) J. Med. Chem. 36(14), 1923–1927.
Plattner et al. (1990) in Drug Discovery Technologies Clark et al (Eds). p. 92–126. Ellis Horwood, Ltd.
Jager et al. (1988) Biochem. 27, 7237–7246.
Uhlmann et al. (1990) Chem. Rev. 90(4), 544–584.
Baurain R. et al. *Targeting of Daunorubicin by Covalent and Reversible Linkage to Carrier Proteins. Lysosomal Hydrolysis and Antitumoral Activity of Conjugates Prepared with Peptidic Spacer Arms*, Durgs Exptl. Clin. Res. IX(4) 303–311 (1983).
Duncan, R. et al. *Anticancer agents coupled to N–(2–Hydroxypropyl) methacrylamide copolymers. I. Evaluation of daunomycin and puromycin conjugates in vitro*, Br. J. Cancer (1987), 55(2), 165–74.
Eugen Uhlmann, et al, "Antisense Oligonucleotides: A New Therapeutic Principle", Chemical Reviews, vol. 90, No. 4, Jun. 1990, 544–579.
Anne Simon Moffat, "Triplex DNA Finally Comes of Age", *Science*, Research News, vol. 252, 1374–1375.
Louis C. Brock, et al., "Selection of single–stranded DNA molecules that bind and inhibit human thrombin", Nature, vol. 355, 6 Feb. 1992, 564–566.
Sudhir Agrawal, et al., "Oligodexynucleoside phosphoramidates and phosphorothioates as inhibitors of human immunodeficiency virus", *Proceedings of the National Academy of Sciences USA*, vol. 85, pp. 7079–7083, Oct. 1988.
Thomas R. Cech, "The Chemistry of Self–Splicing RNA and RNA Enzymes", Science, vol. 236, 1532–1539, 19 Jun. 1987.
William S. Marshall, et al., "Inhibition of human immunodeficiency virus activity by phosphorodithioate oligodeoxycytidine", *Proceedings of the National Academy of Sciences USA*, vol. 89, pp. 6265–6269, Jul. 1992.

Wei–Chiang Shen, et al., "Conjugation of poly–L–lysine to albumin and horseradish peroxidase: A novel method of enhancing the cellular uptake of proteins", *Proceedings of the National Academy of Sciences USA*, vol. 75, pp. 1872–1876, Apr. 1978.
George Y. Wui, et al., "Specific Inhibition of Hepatitis B Viral Gene Expression in Vitro by Targeted Antisense Oligonucleotides", *The Journal of Biological Chemistry*, vol. 267, No. 18, Jun. 28, 1992, pp. 12436–12449.
Reiko T. Lee, et al, "New Synthetic Cluster Ligands for Galactose/N–Acetylgalacto–samine–Specific Lectin of Mammalian Liver", *Biochemistry 1984*, 23, 4255–4261.
E. Bonfils, et al., "Drug targeting: synthesis and endocytosis of oligonucleotide–neoglycoprotein conjugates", *Nucleic Acids Research*, vol. 20, No. 17, 4621–4629.
Andre Trouet, et al., "A covalent linkage between daunorubicin and proteins that is stable in serum and reversible by lysosomal hydrolases, as required for a lysosomotropic drug–carrier conjugate: In vitro and in vivo studies", Proc. Natl. Acad. Sci. USA 79:626–629 (1982).
R. Duncan, et al., "Biological Evaluation of Soluble Macromolecules as Bioreversible Drug Carriers", Bioreversible Carriers in Drug Design, E. B. Roche, ed. Pergamon Press, New York, 1987, pp. 196–213.
Ching–Hsuan Tung, et al., "Preparation of Oligonucleotide––Peptide Conjugates", *Bioconjugate Chemistry*, 1991, 2, 464–465.
Gary E. Means, et al., "Chemical Modifications of Proteins: History and Applications", *Bioconjugate Chemistry*, 1990, 1, 2–12.
Charles R. Petrie, et al., "An Improved CPG Support for the Synthesis of 3'–Amine–Tailed Oligonucleotides", *Bioconjugate Chemistry*, 1992, 3.
Michael W. Reed, et al., "Acridine–and Cholesterol–Derivatized Solid Supports for Improved Synthesis of 3'–Modified Oligonucleotides", *Bioconjugate Chemistry*, 1991, 2.
Jeanette C. Roberts, et al., "Using Starburst Dendrimers as Linker Molecules to Radiolabel Antibodies", *Bioconjugate Chemistry*, 1990, vol. 1, No. 5.

(List continued on next page.)

Primary Examiner—Mindy Fleisher
Assistant Examiner—Philip W. Carter
Attorney, Agent, or Firm—Klein & Szekeres

[57] ABSTRACT

A covalently linked conjugate of an oligonucleotide (ODN) with a peptide and a carrier or targeting ligand (ODN-peptide-carrier) includes a therapeutic oligonucleotide which is capable of selectively binding to a target sequence of DNA, RNA or protein inside a target cell. The ODN is covalently linked to a peptide which is capable of being cleaved by proteolytic enzymes inside the target cell. The peptide, in turn is covalently linked to a carrier or targeting ligand moiety which facilitates delivery of the entire ODN-peptide-carrier conjugate into the cell, and preferably into a specific target tissue type. Inside the cell, the peptide is cleaved, releasing the ODN which, by binding to the target DNA, RNA or protein sequence, brings about a beneficial result.

12 Claims, 10 Drawing Sheets

OTHER PUBLICATIONS

Mitree M. Ponpipom, et al., "Cell–Specific Ligands for Selective Drug Delivery to Tissues and Organs", *Journal of Medical Chemistry*, 1981, vol. 24, No. 12.

Robert D. Hinrichsen, "3–Modified antisense oligodeoxyribonucleotides complementary to calmodulin mRNA alter behavioral responses in Paramecium", *Proceedings of National Academy of Sciences USA*, vol. 89 pp. 8601–8605.

Charles R. Cantor, et al., "Oligonucleotide Intractions. III. Circular Cichroism Studies of the Conformation of Deoxyoligonucleotides", *Biopolymers*, vol. 9, pp. 1039–1077, 1990.

Christopher P. Stowell, et al., "Preparation of Neoglycoproteins Using 2–Imino–2–methoxyethyl 1–Thioglycosides", Methods in Enzymology, 1982, Vol. 83, pp. 278–288.

O. S. Fedorova, et al., "Complementary addressed modification of double–stranded DNA within a ternary complex", FEBS Letters, vol. 228, No. 2, 273–276.

Valentin V. Vlassov, et al., "Modified Oligodeoxyribo––nucleotides–Sequence–specific chemical modifications of double–stranded DNA with alkylating oligodeoxyribonucleotide derivatives", *Gene, Elsevier Science Publishers B.V.*, 72 (1988) 313–322.

ODN-PEPTIDE LINKER

ODN represents a therapeutic oligonucleotide drug.

PEPTIDE represents an amino acid sequence which is readily cleaved in lysosomes.

A, B, and C represent crosslinking funcitonal groups.
   In this case A = iodoacetamide, B = thiol, and C = amino

Figure 4.

Class 1. Surfactant Carriers

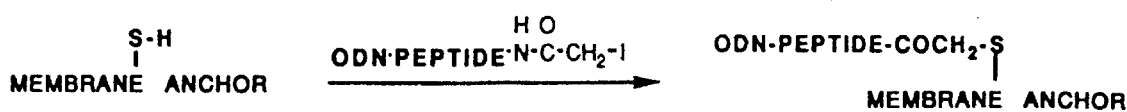

Class 2. Polyamine Carriers

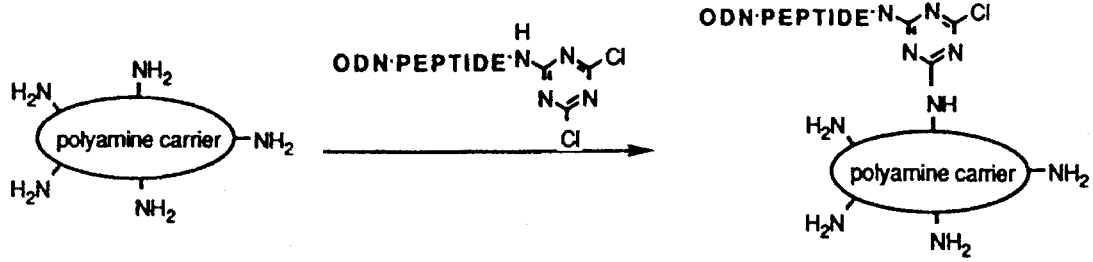

Class 3. Targeting Ligands

Method A (Indirect Synthesis):

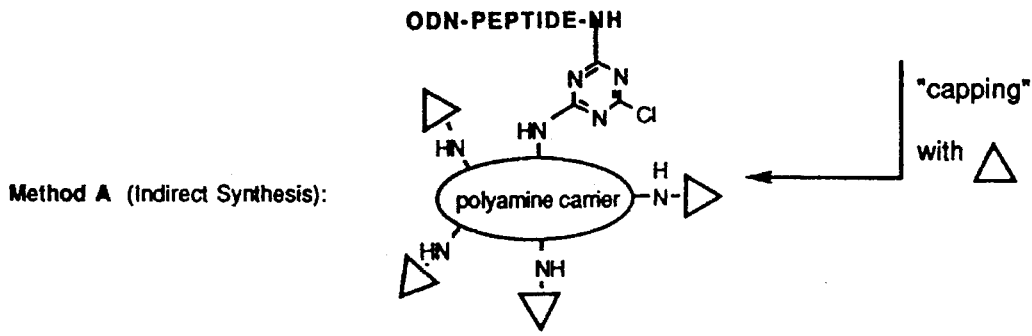

Method B (Direct Synthesis):

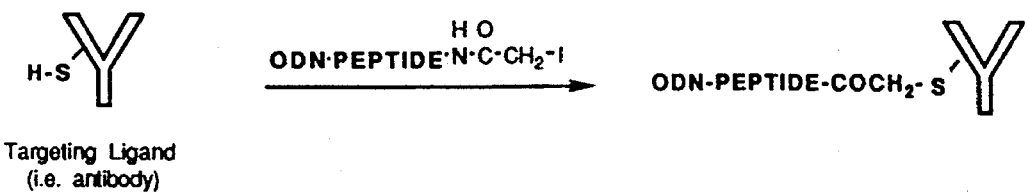

Targeting Ligand
(i.e. antibody)

---

ODN represents a therapeutic oligonucleotide drug.

PEPTIDE represents an amino acid sequence which is readily cleaved in lysosomes.

 represents a "membrane recognition element". For example, sugars.

Figure 7.

Hydroxyprolinol Monomers

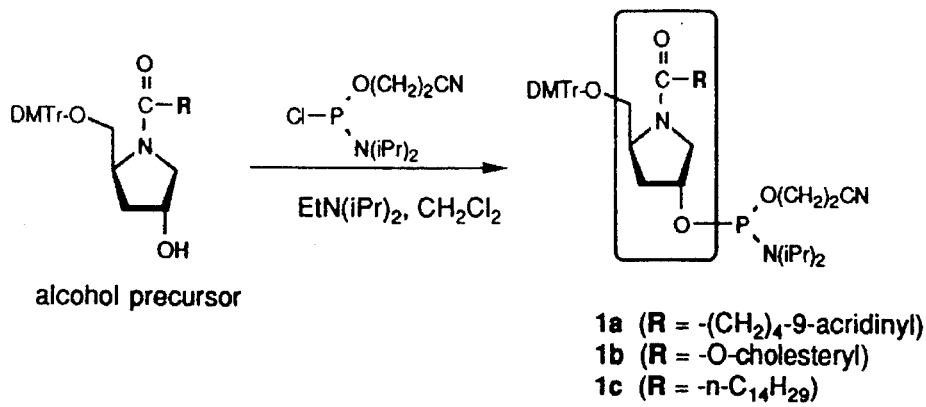

1a (R = -(CH$_2$)$_4$-9-acridinyl)
1b (R = -O-cholesteryl)
1c (R = -n-C$_{14}$H$_{29}$)

Alkanol Monomers

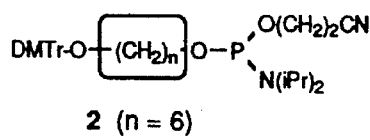

2 (n = 6)

Polyethylene Glycol Monomers

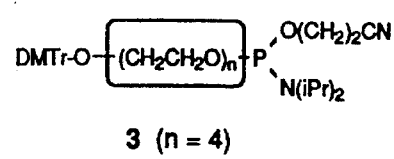

3 (n = 4)

---

Polymer Synthesis:

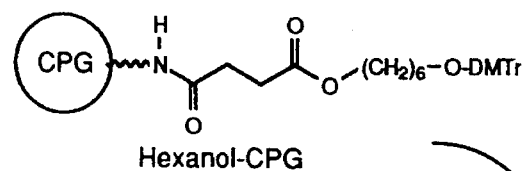

Hexanol-CPG

Repeat Synthesis Cycle (n times):
1) remove DMTr (dichloroacetic acid)
2) activate monomer with tetrazole
3) couple activated monomer to free hydroxyl
4) oxidize phosphorus with I$_2$ / pyridine

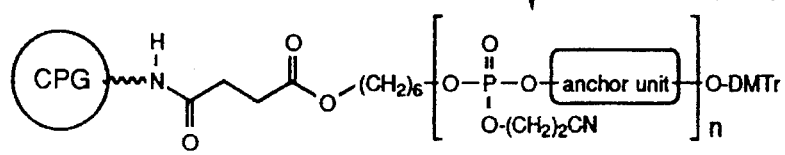

1) additional synthesis cycle using thiol amidite
2) ammonia hydrolysis
3) HPLC purification
4) reduce disulfide (DTT)

MEMBRANE ANCHOR ≡ 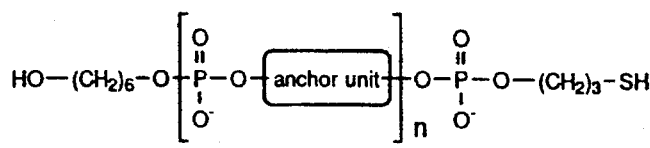

Figure 9.
Polyethyleneimine
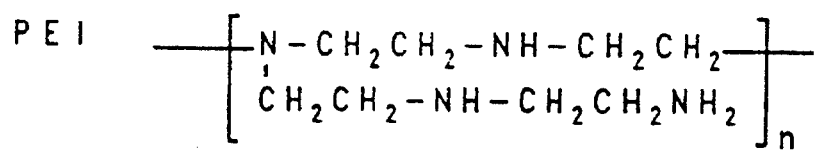
Poly-L-Lysine
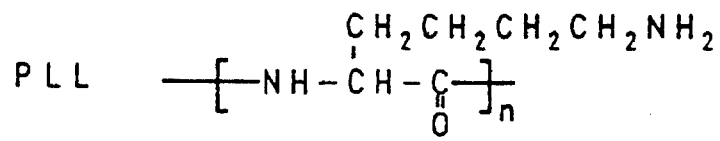
Starburst Dendrimers
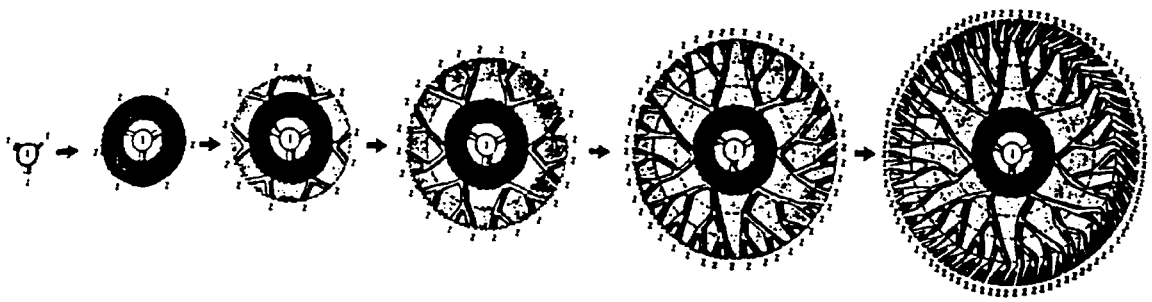

Figure 10.
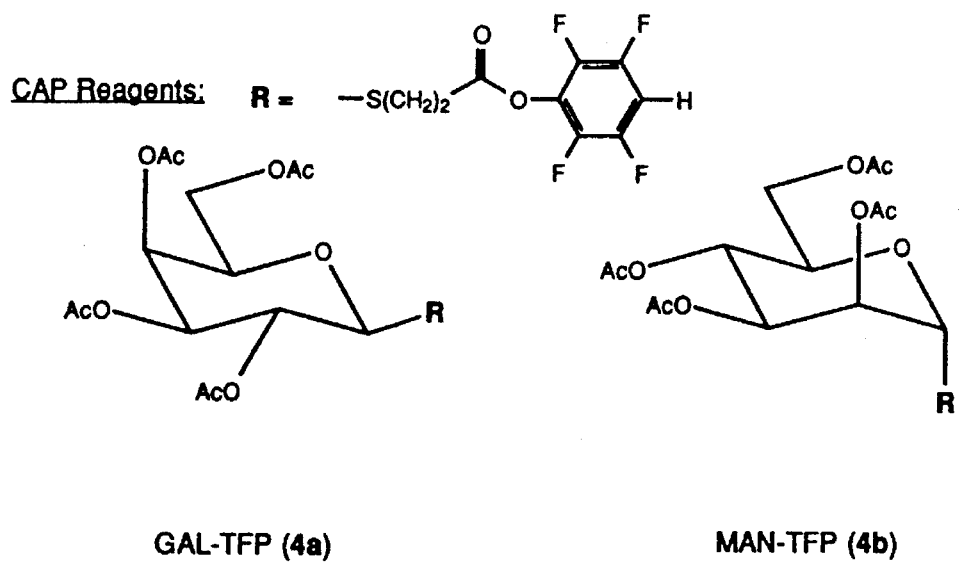
GAL-TFP (4a)  MAN-TFP (4b)
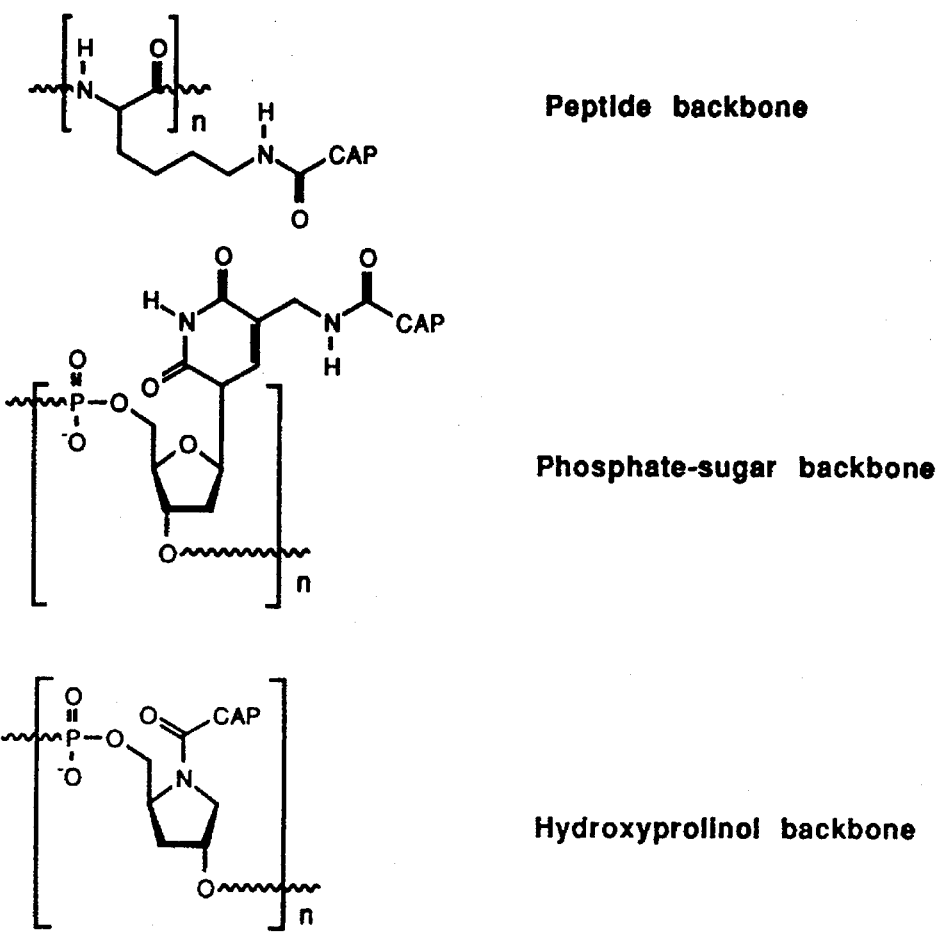
Peptide backbone
Phosphate-sugar backbone
Hydroxyprolinol backbone

PEPTIDE LINKERS FOR IMPROVED OLIGONUCLEOTIDE DELIVERY

TECHNICAL FIELD

The invention relates to pharmaceutical compositions containing oligonucleotides (ODNS, having 5–100 nucleotides) (such as "antisense" or "antigene" agents) which act by binding to intracellular molecular targets, and which, for efficient delivery to a target DNA, RNA or protein, are covalently linked through a cleavable peptide moiety to a carrier moiety, which facilitates delivery of the ODN to the cytosol.

DESCRIPTION OF BACKGROUND ART

Antisense oligodeoxynucleotides (ODNs) provide a means to sequence specifically inhibit synthesis of distinct proteins within a cell. For a review reference is made to Uhlmann, E. and Peyman, A., (1990) Antisense oligonucleotides: a new therapeutic principle, *Chem. Rev.*, 90, 543. The prior art is aware that by targeting mRNA sequences which code for proteins associated with disease (for example, viral proteins), antisense ODNs can have a therapeutic effect. The exquisite specificity of DNA:RNA hybridization is expected in the art to provide drugs with fewer toxic side effects. Although the antisense oligonucleotide therapeutic principle is very appealing from a theoretical viewpoint, the state of the art is that because of their high cost and low molar potency, these agents are currently not used as effective antiviral drugs. Moreover, the highly charged ODNs do not enter the cytoplasm of cells easily, and therefore many approaches have been taken in the prior art to improve delivery of ODN drugs across membrane barriers.

Antigens oligonucleotides are another class of sequence specific drugs which can inhibit protein synthesis. For a review reference is made to Moffat, A. S. (1991) Triplex DNA Finally Comes of Age, *Science* 252, 1374. Antigene ODNs bind to duplex DNA as a third strand and can inhibit transcription of mRNA. In theory, antigene ODN drugs should be more potent than antisense ODN drugs since there is only one genetic target (DNA). Currently this technology is limited by the number of gene targets which triple strand binding ODNs can recognize, but the field is rapidly advancing. The potency of antigene ODNs can be further enhanced by modification with functional groups that react with the duplex DNA target strands. Alkylating groups or cleaving groups which are targeted by antigene ODNs have the potential to permanently inactivate specific genes, thereby providing a rational base for curing disease. Since these ODNs act in the nucleus of cells, they must also be delivered across membrane barriers.

Protein binding oligonucleotides are another potential class of therapeutic. These are oligonucleotides that bind to specific proteins. Recently, it has been reported that single stranded ODNs can be isolated which bind to protein targets in a sequence specific manner and inhibit protein function. This is described in the reference article Bock, et al., (1992) Selection of single-stranded DNA molecules that bind and inhibit human thrombin, *Nature*, 355, 564. Other examples of protein binding ODNs are homopolymers of phosphorothioates (Agrawal, S. Goodchild, J., Civiera, M. P., Thornton, A. H. Sarin, P. S. and Zamecnik, P. C., (1988) Oligodeoxynucleoside phophoramidates and phosphorothioates as inhibitors of human immunodeficiency virus, *Proc. Natl. Acad. Sci, U.S.A.*, 85, 7079) or phosphorodithioates (Marshall, W. S., Beaton, G., Stein, C. A., Matsukura, M., and Caruthers, M. H. (1992) Inhibition of human immunodeficiency virus activity by phosphorothioate oligodeoxycytidine, *Proc. Natl. Acad. Sci. U.S.A.*, 89, 6265) which have been shown to bind to viral reverse transcriptase and inhibit HIV replication. A problem encountered in connection with oligonucleotides which target intracellular proteins is delivery across cellular membranes.

Ribozymes are another class of oligonucleotides which can sequence specifically catalyze the hydrolysis of target RNA strands. For a description see Cech, T. R. (1987) The chemistry of self-splicing RNA and RNA enzymes, *Science* 236, 1532. The prior art has already proposed using these catalytic, RNA based "scissors" as therapeutic agents. The problem again is the delivery of the ribozyme oligonucleotides across cellular membranes.

In light of the foregoing it appears desirable to improve delivery of ODN drugs from the extracellular media (i.e. serum) into the cytosol of cells. Polyanionic ODNs cross membranes poorly and can be degraded by nucleases before reaching their ultimate site of action (the cytoplasm or nucleus of cells). Thus, poor bioavailability is a major reason for the low potency of ODN drugs. Therefore it is desirable to take advantage of endocytosis; an uptake pathway which cells use to bring macromolecules across the plasma membrane and deliver them to lysosomes. Lysosomes are low pH, membrane bound vesicles which contain the hydrolytic enzymes necessary to digest the concentrated macromolecules.

Further, it is desirable to improve the potency of ODN drugs by targeting them to specific tissue types. There has been a significant research effort in the prior art on design of cleavable linking groups to attach drugs to targeting ligands. The "flagship" targeting ligands for tissue specific targeting of drugs are monoclonal antibodies. These compounds can be "engineered" to bind to specific cell-surface receptors (antigens) which are rapidly endocytosed. Therefore, it is desirable to improve the potency of ODN drugs by increasing transport of ODNs across cellular membranes and further to improve potency by targeting the nucleic acid specific ODN drugs to cell specific receptors through choice of appropriate ligands. Thus "matched sets" of nucleic acid specific ODNs and tissue specific targeting ligands are expected to provide drugs with higher therapeutic index than traditional pharmaceuticals.

SUMMARY OF THE INVENTION

The invention described here pertains to specific drug-linker-carrier compositions wherein the drug is a therapeutic ODN and the linker is a lysosome sensitive peptide. Within the scope of the invention are several versatile chemical methods for the synthesis of ODN-peptides. These methods enable the construction of ODN-peptides which can be linked to virtually any lysosomotropic carrier or targeting ligand of choice. The modular nature of the chemistry facilitates variation of the therapeutic ODN, the peptide, and the carrier. The delivery system can be "fine-tuned" to increase the potency and therapeutic index of oligonucleotide based drugs.

More specifically, the three components of therapeutic agents of the invention are (1) therapeutic ODN;

(2) a peptide linker which must cleave after the therapeutic ODN is delivered in order to release the therapeutic ODN, and a (3) carrier, which facilitates transport of the ODN to the desired site of action.

The foregoing three components are covalently linked in accordance with the present invention.

With regard to the therapeutic ODN, it is noted that state-of-the-art antisense and antigene ODNs are within the scope of the invention, which may be chemically modified or unmodified as compared to the "natural" unmodified DNA constituents normally occuring in living cells.

The nature of the three components of the ODN-peptide-carrier conjugate molecule of the present invention is described in detail and with reference to specific examples, in the following Detailed Description of the Invention.

BRIEF DESCRIPTION OF THE DRAWINGS

FIG. 4 illustrates preferred methods of synthesis for three classes of lysosomotropic ODN-peptide-carrier conjugates.

FIG. 7 shows the structure and synthesis of thiol modified "membrane anchors" which can be used as surfactant carriers for ODNs.

FIG. 9 shows the structure of preferred polyamine carriers.

FIG. 10 shows galactose containing compounds which can be used to construct hepatocyte specific targeting ligands for ODNs.

DETAILED DESCRIPTION OF THE INVENTION

The therapeutic ODNs utilized in the present invention, are the "active agents" in the sense that after release from the ODN-peptide-carrier conjugate, the ODNs bind to a desired DNA, RNA or protein to bring about the desired therapeutic action. Inasmuch as therapeutic ODNs are per se well-known in the art, and are subject to numerous patent and scientific literature references, their detailed description is not necessary here. By way of summary it is stated here that antisense ODNs, antigene ODNs, protein binding ODNs, and ribozymes are within the scope of the present invention.

Moreover, the ODN components of the ODN-peptide-carrier conjugates of the invention may contain all natural nucleotide building units, or may contain synthetic nucleotides, modified nucleotides such as nucleotides modified by attachment of groups to the heterocyclic bases, sugar or phosphate moieties, or α-nucleotides, and nucleotides wherein the "natural" phospho-diester linkage has been modified. RNA based therapeutics, such as ribozymes, are also included under the general abbreviation "ODN".

The criterion with respect to the therapeutic ODN component of the ODN-peptide-carrier conjugate of the present invention is that the ODN must be capable of selective binding to a target DNA, RNA, or protein within a target cell, to bring about a desired biological effect.

. The carriers utilized in the covalently linked therepeutic ODN-peptide-carrier conjugate molecules of the invention are lysosomotropic agents. These are substances which are taken up selectively into lysosomes. Endocytosis is the primary cellular mechanism by which these agents are transported from the extracellular media to the lysosomes. The effect of lysosomotropic drug carriers is to concentrate drug inside the cell. The drug must be released from the carrier in order to diffuse to its ultimate intracellular target.

Figure 1:
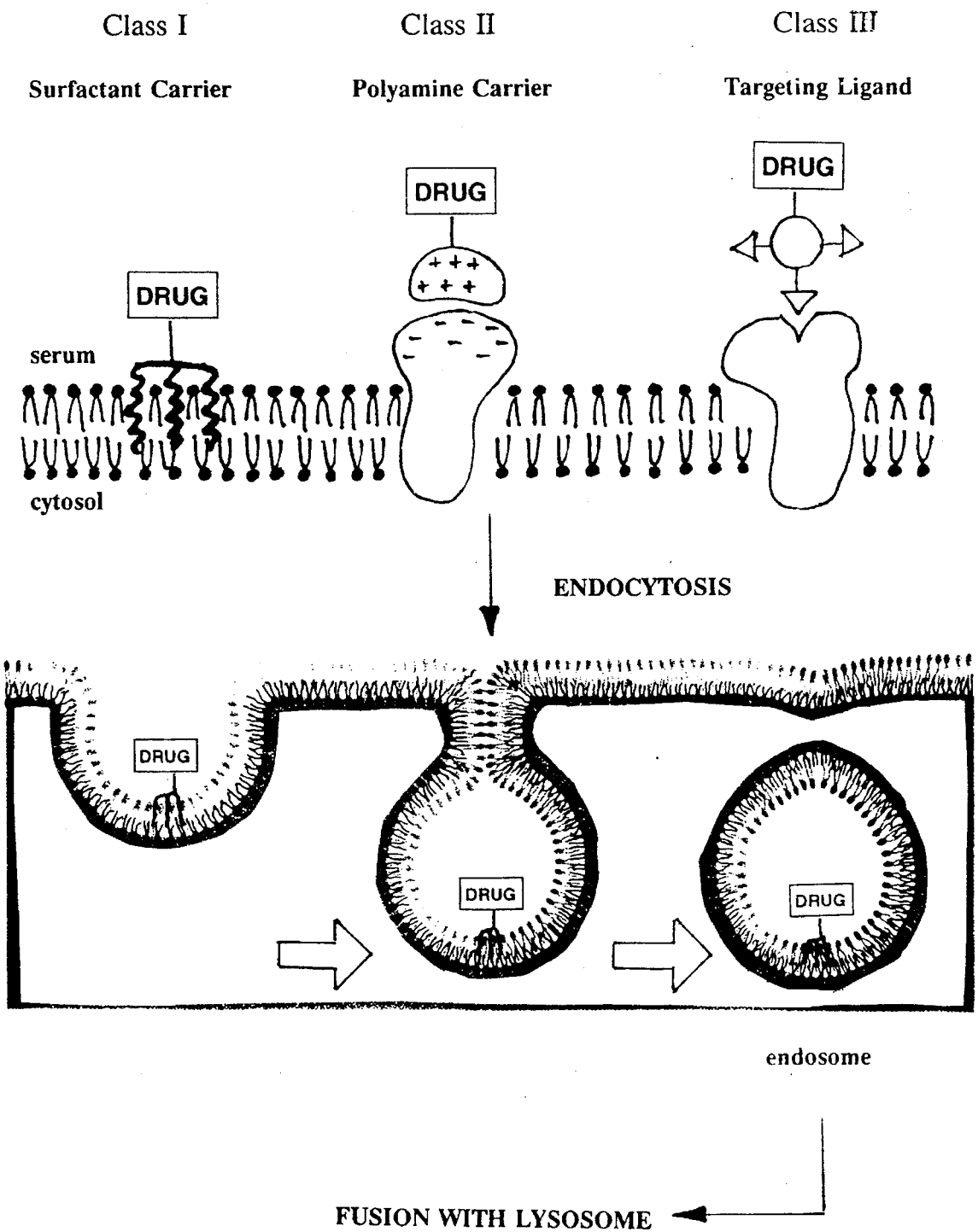
FIG. 1 illustrates the membrane binding mechanism of the three classes of lysosomotropic drug carriers applicable to the invention.
Figure 2:
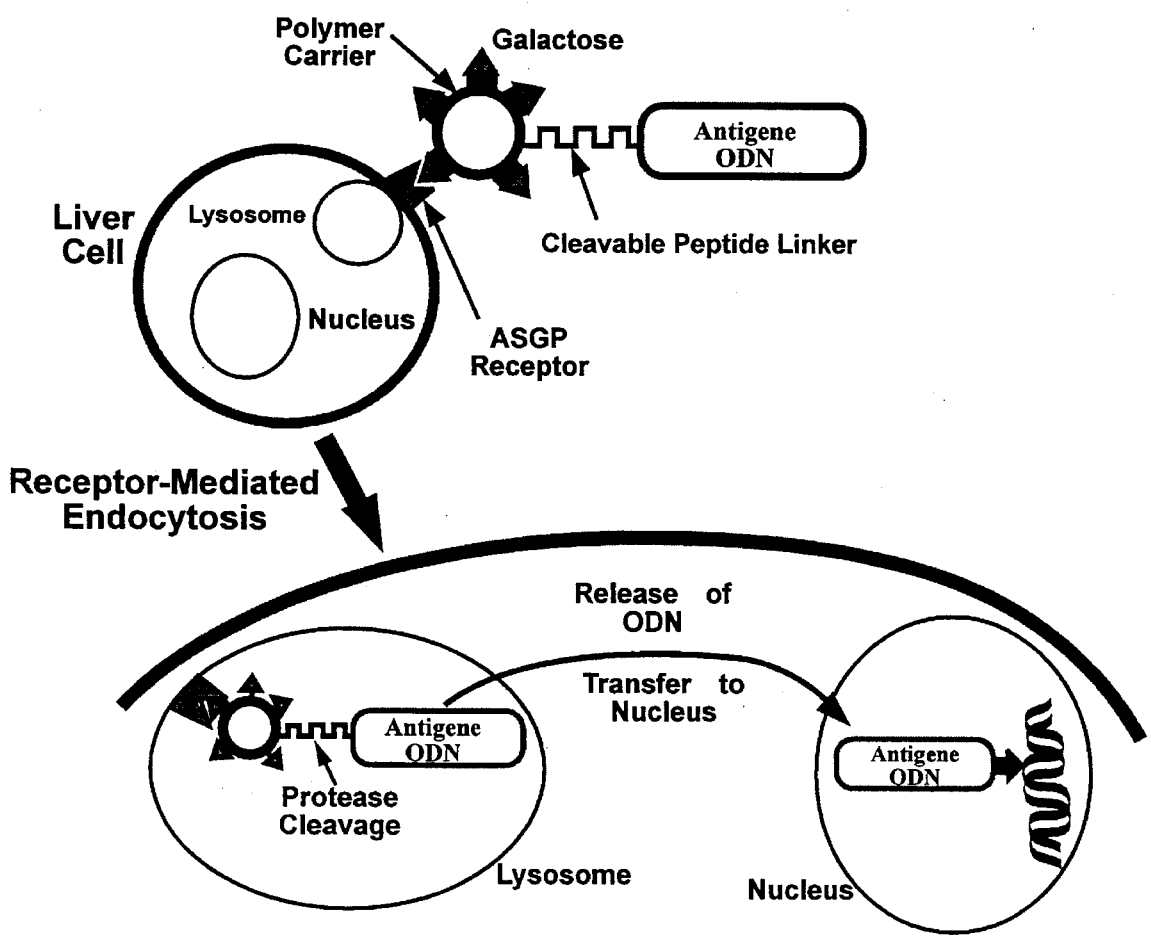
FIG. 2 is a schematic illustration of the mechanism by which the ODN-peptide-carrier conjugates enter the cell and release the drug. In the illustration, the lysosomotropic carrier (galactose coated polymer) specifically targets hepatocytes. The antigene (or antisense) ODN is designed to sequence specifically inhibit synthesis of vital proteins in HBV infected cells.

Three categories of lysosomotropic agents which are utilized in the invention are illustrated in FIG. 1. They are classified according to the mechanism by which they bind to the plasma membrane and by the cellular specificity of that binding. After binding to the plasma membrane, all three categories of agents are delivered to the lysosome by endocytosis.

A first category (Class 1) of lysosomotropic agents are surfactant carriers. These are molecules with surfactant properties. The nonioinic detergent Triton WR-1339 is an example of this class of agent. Highly lipophilic "membrane anchors", such as cholesterol or lipids, are another example of this class of carrier. Surfactant carriers interact with the plasma membrane of cells and are endocytosed by a process termed "pinocytosis" or "fluid-phase endocytosis". This process, which is per se well known in the art is illustrated in FIG. 1.

A second category (Class 2) of lysosomotropic agents are polyamine carriers. Specifically, cationic macromolecules have been shown to be lysosomotropic. The best known of this class of agent is poly-L-lysine (PLL). Moreover, it is known that the cellular uptake of proteins and other macromolecules can be enhanced by conjugation to PLL or other polyamines Shen, W.-C., and Ryser, H. J.-P. (1978) Conjugation of poly-L-lysine to albumin and horseradish peroxidase: A novel method of enhancing the cellular uptake of proteins. *Proc. Natl. Acad. Sci. U.S.A*, 75, 1872. PLL is internalized by a process described as "non-specific adsorptive pinocytosis". The presumed mechanism of this is illustrated in FIG. 1.

A third category (Class 3) of lysosomotropic agents are targeting ligands. Of particular interest to the present invention are receptor-specific targeting ligands. In the context of this invention, targeting ligands are defined as molecules containing specific conformations of functional groups which "fit" into recognition sites on membrane bound receptors. The size, shape (conformation), charge density, lipophilicity, and location of hydrogen bonding functional groups are critical properties which ensure recognition by specific membrane receptors. Molecular fragments such as sugar groups can serve as "membrane recognition elements". Certain combinations and conformations of these elements are recognized and bound by cell-surface receptors. The ligand-receptor complex is internalized by receptor-mediated endocytosis. A wealth of knowledge has unfolded regarding ligands (including ODNs) which are endocytosed by this receptor-mediated process. As of this date, several hormones, growth factors, proteins (e.g. low-density lipoprotein (LDL), $\alpha_2$-macroglobin, antibodies, transferrin, vitellogenin, and toxins) and viruses have been shown to enter cells by this receptor-mediated process.

Many of these receptors are "non-cell specific" (i.e. they are found on a majority of cell types). An example would be transferrin, a protein that carries iron in the blood. All actively metabolizing cells have transferrin receptors which endocytose.

"Tissue specific" receptors are those that are found in a certain sub-population of cells within an organism. In order to be suitable targets for ligand-drug conjugates, these receptors must also be rapidly endocytosed. Provided below are illustrative examples of tissue specific receptors which fit these criteria. It should be noted that the "tissue specificy" of targeting ligands as drug carriers is not absolute, and is ultimately determined by biodistribution in suitable animal models.

Galactose receptor on hepatocytes. If sialic acid residues are removed from the oligosaccharide side chains of glycoproteins, terminal galactose residues are exposed which are recognized by a specific receptor [known as asialoglycoprotein (ASGP) receptor] on hepatocytes. This system is very efficient and well understood. As early as 1971, it was proposed to use asialoglycofetuin as a carrier "to specifically induce the hepatic uptake of other substances such as drugs". Recently, it has been demonstrated that conjugates of poly-L-lysine and asialoglycoproteins can form complexes with antisense oligonucleotides to give improved antiviral potency against hepatitis B (see Wu, G. Y., and Wu, C. H. (1992) Specific inhibition of hepatitis B viral gene expression in vitro by targeted antisense oligonucleotides, *J. Biol. Chem.* 267, 12436).

The geometric constraints of the ASGP binding site have been extensively studied using synthetic, galactose containing "cluster ligands" Lee, R. T., Lin, P., and Lee, Y. C. (1984), New synthetic cluster ligands for galactose/N-acetylgalactosamine-specific lectin of mammalian liver, *Biochemistry* 23, 4255. It has been postulated that three galactose-binding sites of the receptor are arranged in space at the vertices of a triangle whose sides are 15, 22, and 25 angstroms. Ligands have been prepared which have binding affinities approaching the complex asialoglycoproteins ($K_d$= ca. $10^{-9}$M).

Less well designed galactose containing ligands also bind to the ASGP receptor, especially when attached to macromolecular carriers. For example, treatment of polyamines such as PLL or PDL with reactive galactose compounds yield "synthetic glycoproteins" which have been used for endocytosis studies. In general, it is advantageous to have multiple galactose "membrane recognition elements" present in these synthetic ligands.

Mannose receptor on macrophages. Mammalian macrophages contain a transport system that binds and internalizes glycoproteins with exposed mannose residues. The components and functioning of this macrophage specific system is similar to the hepatocyte specific system described above. A tri-mannosyl ligand has been shown to be an effective substrate for this receptor.

Mannose-6-phosphate receptor on monocytes. Monocytes and macrophages contain a membrane lectin which specifically bind mannose-6-phosphate bearing glycoproteins. Recently, it has been shown that uptake of oligonucleotides into macrophages can be enhanced by conjugation to 6-phosphomannosylated serum albumin. For a description see Bonfils, E., Depierreux, C., Midoux, P., Thuong, N. T., Monsigny, M., and Roche, A. C. (1992) Drug Targeting: synthesis and endocytosis of oligonucleotide-neoglycoprotein conjugates, *Nucleic Acids Res.* 20, 4621.

Polyanion receptor on macrophages. Polyanionic macromolecules such as acetylated LDL, maleylated albumin, and sulfated polysaccharides are recognized by a specific receptor in mammalian macrophages.

CD3 antigen on T-lymphocytes. The human CD3 ("T3") antigen is a receptor found on human T-cells. Anti-CD3 monoclonal antibodies are available which recognize the antigen. Such antibodies have been used clinically for the prevention and treatment of graft vs. host disease and for treatment of T-cell malignancies.

The nature of the linking molecule, which covalently links the therapeutic ODN (drug) with the carrier (targeting ligand) is important. The therapeutic ODN (drug) must be released from the targeting agent in order to reach its ultimate site of action in the cell. Analogy in the prior art are monoclonal antibody-drug conjugates which are internalized and degraded in the lysosomes to release the drug (or drug-linker fragment). Lysosome-sensitive linkers have therefore been explored in the prior art for use in these ligand-drug conjugates.

There are known in the prior art several cleavable peptide linkers capable of enlarging delivery of small molecular weight, cytotoxic drugs via macromolecular carrier molecules. Such peptides include leu-ala-leu and ala-leu-ala-leu. The latter two have been known to release free drug from a BSA carrier when treated with lysosomal enzymes (Trouet, A., Masquelier, M., Baurain, R., and Deprez-de Campaneere, D. (1982), A covalent linkage between daunorubicin and proteins that is stable in serum and reversible by lysosomal hydrolases, as required for a lysosomatropic drug-carrier conjugate: In vitro and in vivo studies, *Proc. Natl. Acad. Sci. U.S.A.* 79, 626).

Another carrier known in the prior art is the synthetic polymer N-(2-hydroxypropyl)methacrylamide (HPMA) which has been extensively studied as a carrier for drugs (for review see Duncan, R., Kopecek, J., and Lloyd, J. B. (1987), Biological evaluation of soluble macromolecules as bioreversible drug carriers, *In Bioreversible Carriers in Drug Design*, (E. B. Roche, Ed.) pp 196–213, Pergamon Press, Elmsford, N.Y.). This carrier (HPMA) has been conjugated to drugs with inter alia, the peptide sequence gly-phe-leu-gly-phe.

The foregoing peptides sequences provide examples of the peptide linkers which can be used in accordance with the present invention. Generally speaking the requirement is that the peptide be covalently linked to both the therapeutic ODN (drug) and to the carrier, (targeting ligand) and that it be cleaved inside the cell after the target is reached, so as to release the therapeutic ODN.

It is noted at this stage of the description of the present invention that whereas there have been several prior art reports of syntheses of ODN-peptide conjugates (for references see Tung, C., Rudolph, M. J., and Stein, S. (1991), Preparation of Oligonucleotide-Peptide Conjugates, *Bioconjugate Chem.* 2, 464), to the best knowledge of the present inventors the concept of utilizing peptides as degradable linkers between carriers (targeting ligands) and therapeutic ODNs is new.

Within the broad teachings of the present invention the following general examples and specific embodiments are provided.

GENERAL EMBODIMENTS

The present invention employs ODN-peptide conjugates wherein the peptide moiety bears a functional group which can be selectively crosslinked to a functional group on lysosomotropic carrier (targeting ligand) molecules. Within this principle, methods are described for preparation of three examplary classes of ODN-peptide-carrier conjugates. The peptide functions as a protease sensitive (cleavable) linker. The peptide sequence is chosen such that it is hydrolyzed by proteases in the lysosomes of the target cells and not by serum proteases.

The ODNs which are released in the lysosomes in accordance with the invention have a therapeutic function. As noted above, the therapeutic ODNs may be modified with groups which improve their binding to the target, improve their stability to nucleases, and/or improve their ability to cross the lysosomal membrane. For example, modification of the 3'-terminus of the ODN has been found to enhance stability to exonucleases, and such 3'-terminus modified ODNs may be advantageously employed in accordance with the invention. Lipophilic modifications of ODNs have been found to enhance membrane transport. Such "lipophilicy modified" ODNs may also be advantageously employed in accordance with the present invention.

It is a feature of the present invention that the ODN is a therapeutic agent which specifically inhibits synthesis or function of proteins which are implicated in a diseased state. Targeting ligands can be chosen to provide selective delivery to diseased cells. The therapeutic-ODN and targeting ligand provide a "matched set" wherein the targeting ligand is chosen to selectively deliver the therapeutic ODNs to those cells which are synthesizing deleterious proteins. Several examples of "matched set" ODN-peptide-ligand combinations are described below which provide therapy for particular diseases.

A specific example of a "matched set" ODN-peptide-ligand conjugate is particularly noteworthy. In this example the therapeutic ODN is an antisense ODN which sequence specifically inhibits synthesis of a protein that is synthesized by hepatocytes infected by Hepatitis B virus (HBV). The targeting ligand is a galactose modified polymer which is specifically recognized and internalized by hepatocytes. The peptide linker is chosen on the basis of its known sensitivity to rat liver lysosomal proteases.

Figure 3:
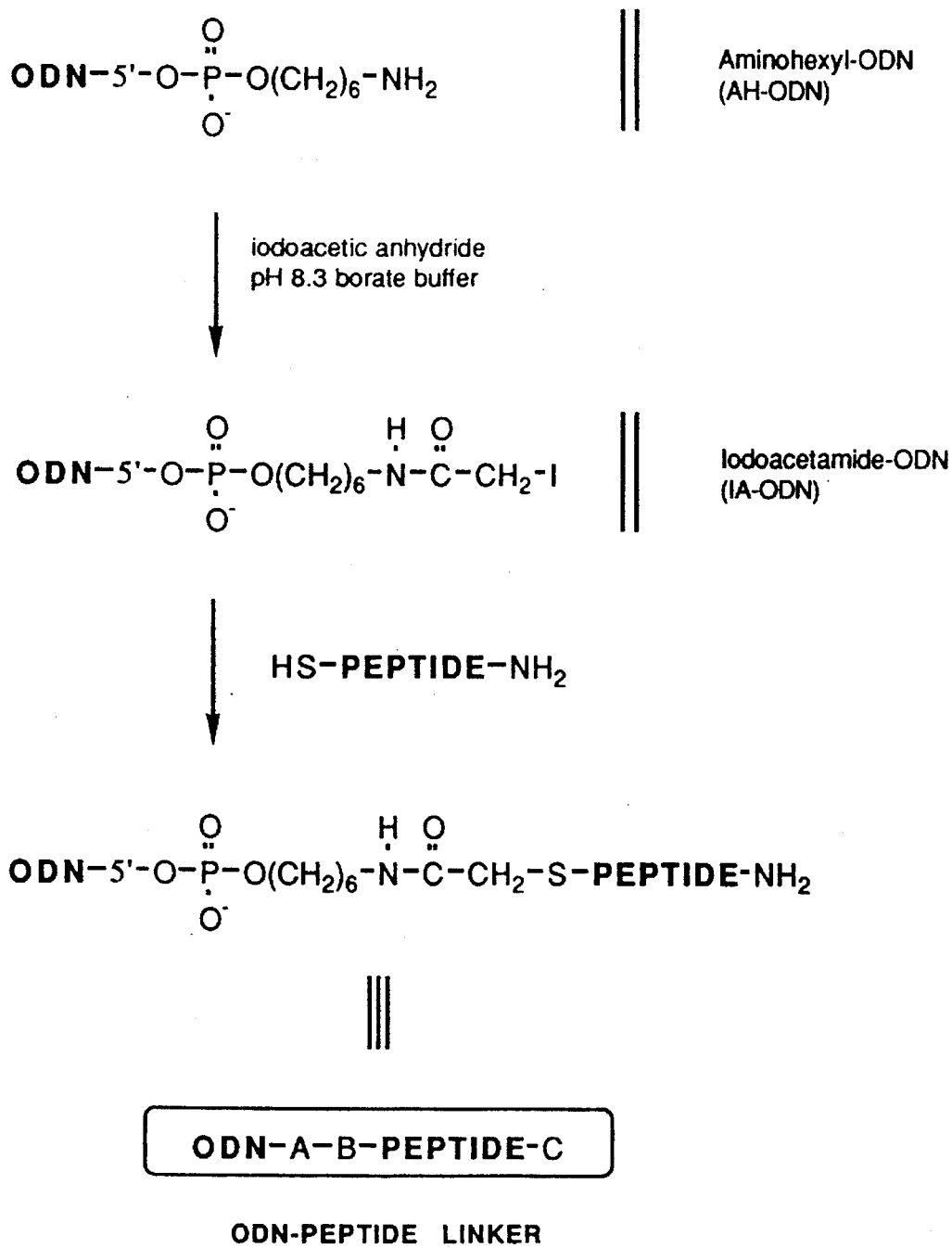
FIG. 3 illustrates the synthetic scheme used for conjugating amine modified ODNs to peptide linkers.

FIG. 3 describes the general structure and method of synthesis for ODN-peptide conjugates which are linked in accordance with the present invention to lysosomotropic carriers. The illustrated method utilizes a therapeutic ODN which has been modified with a suitable electrophilic or nucleophilic linker group (A). Such modified ODNs are readily prepared using standard automated techniques. The purified ODN is treated with a peptide that bears two crosslinkable groups (B) and (C) with different reactivity such that (A) reacts with (B), yet (C) remains free for further crosslinking reactions. The resulting "crosslinkable" ODN-peptide is purified and used as a versatile intermediate for conjugation of ODNs to various lysosomotropic carrier molecules via the peptide linking arm. Three general classes of therapeutic conjugates can be prepared from these "crosslinkable" ODN-peptides as illustrated in FIG. 4.

Referring now to FIG. 4 the Class 1 conjugates are the simplest ODN-peptide-carrier constructs. In this case, the lysosomotropic carriers are "membrane anchors" or "surfactants" which have affinity for the plasma membrane of the cell. This non-specific mechanism may be advantageous for cell culture systems, where it is desired to target every cell. Although such conjugates do not provide cell specific targeting, they improve potency of ODNs by increasing the rate of transport across the plasma membrane. The ODN conjugates are delivered to the lysosomes where the peptide linkers are hydrolyzed to release the active ODN drugs.

These conjugates can be prepared in accordance with the present invention through sulfhydryl-iodoacetamide coupling chemistry. In the example shown on FIG. 4, the ODN-peptide conjugate of FIG. 3 has already been reacted with iodoacetic anhydide to provide the iodoacetamide derivative. This is reacted with a "membrane anchor" group having a free thiol group to provide the ODN-peptide-$COCH_2$—S— membrane anchor product. The chemistry utilizing such iodoacetamide derivatives is very versatile, due to the extreme nucleophilicity of the sulfhydryl group and the extreme electrophilicity of the iodoacetamide.

The Class 2 ODN-peptide conjugates illustrated in FIG. 4 are analogous to the ODN-PLL conjugates described above. However, in accordance with the present invention because a degradable peptide linker is used, non-natural polyamines less toxic than PLL are preferably substituted for the poly-L-lysine carrier. This class of conjugates can be further modified with targeting ligands to provide Class 3 conjugates.

Cyanuric chloride coupling chemistry is illustrated for the preparation of these conjugates as the preferred method for coupling amine modified ODNs to amine containing polymers.

The Class 3 conjugates illustrated on FIG. 4 utilize receptor specific targeting ligands. This class of conjugates is the most versatile in that the biophysical properties can be "fine-tuned" to optimize potency of the ODN drug. The number of targeting ligands, size of the carrier, or charge of the complex can be varied to optimize cellular uptake. With complex galactose containing ligands such as AsOR, only one ligand is necessary whereas when the ligand ("membrane recognition element") in a simple molecule, such as galactose, then binding of several ligands to the ODN-peptide molecule would be advantageous. By attaching nucleic acid specific ODN drugs to tissue-specific ligands, "matched sets" are created which dramatically improve ODN potency and therapeutic index.

Two methods are described for preparation of these conjugates. Method A involves modification of the Class 2 conjugates with a reactive form of a "membrane recognition element". Method B involves direct reaction of an ODN-peptide with a pre-formed targeting ligand. In the Method B example illustrated on FIG. 4 the peptide is modified with a reactive iodoacetamide group and the targeting ligand is a sulfhydryl modified monoclonal antibody.

Other Constructs. Degradable polyamines such as PLL can also be used in accordance with the present invention. For example, reaction of cyanuric chloride activated ODNs with PLL provides a novel method for preparation of ODN-PLL conjugates (Class 2). Since PLL is itself a cleavable peptide, the specially designed linking peptide sequences of the invention are not necessary in this case, because PLL acts as the cleavable peptide link. Treatment of this novel class of ODN-PLL conjugates with ligands or "membrane recognition elements" (such as sugars) provides Class 3 conjugates.

Preparation of MODEL ODN-Peptide Conjugates

Certain features of the present invention are demonstrated by model ODN-peptide conjugates, illustrated in FIG. 3, which can be prepared in several ways. With reference to FIG. 3, the ODN is attached (linked) to the peptide through a "branching or linking group". The branching or linking groups (A)–(C) are available in the art with a variety of chain lengths and reactive crosslinking functionality. Therefore, a vast array of linking groups and crosslinking groups on the ODN and peptide can be chosen. For the purpose of this description, branching or linking groups are defined as molecular fragments which connect, or have the ability to connect, two other molecular functions (in this case the ODN with the peptide). The most versatile of these linking groups are known as "heterobifunctional linkers". These linkers have two different crosslinking groups which can react in a stepwise fashion. Many of these linkers are commercially available from biotechnology supply companies (e.g. Pierce Chemical Company).

The use of bifunctional and heterobifunctional linkers for crosslinking and immobilization of proteins has been reviewed (Means, G. E. and Feeney, R. E. (1990), Chemical Modification of Proteins: History and Applications, *Bioconjugate Chem.* 1, 2.). The concepts presented in this review are also applicable to crosslinking and immobilization of ODNs. Linker arms and crosslinking chemistry for ODNs are also generally known in the art. Generally, these linker groups are composed of unreactive spacer groups and two crosslinking groups with different reactivity.

FIG. 3 illustrates the conjugation chemistry which is currently the most efficient and versatile route to ODN-peptide-ligand conjugates. The specific conjugation chemistry which is used in this embodiment for attaching ODN group (A) to peptide group (B) is novel. The method involves conjugation of an ODN bearing an electrophilic crosslinking group to a peptide which bears two nucleophilic groups ((B) and (C)) of differing reactivity. The resulting ODN-peptide conjugate is prepared in such a manner that a nucleophilic "handle" (C) remains on the peptide. This group is used to further attach the lysosomotropic carrier to the peptide portion of the ODN-peptide conjugate. The peptide is therefore also used as a heterobifunctional linker. Whereas heterobifunctional linking groups have been known in the art, ODN-peptide conjugates which are themselves "cross-linkable" are believed to be novel.

Others, skilled in the art of bioconjugate chemistry and with this disclosure, will be able to prepare conjugates using different crosslinking chemistry which utilize peptides as attaching groups between ODNs and carriers and targeting ligands.

The ODN-peptides described here as models were not designed for use as cleavable linkers. They are included in this application to illustrate the conjugation chemistry which has been developed in accordance with the present invention. In addition, the model peptides were used to demonstrate that peptide linkers can be selectively cleaved by proteases without affecting the ODN.

Specifically, the exemplary chemistry is illustrated using two different MODEL ODNs:

ODN1:  $H_2N-(CH_2)_6-O-PO_2^--5'O-CTCCATCT-TCGTCACA$

ODN1 Sequence ID No. 8 is a 5'-hexylamine modified 16-mer ODN with a sequence complementary to the initiation codon region of the mRNA transcript for the Hepatitis B surface antigen in Hep3B cells.

ODN2:  $H_2N-(CH_2)_6-O-PO_2^--5'O-TAATTAT-TCAGCCATTTATTATTAGTT-O-PO_2^--O-(CH_2)_6$

ODN2 Sequence ID No.: 9 is a 3'-hexanol, 5'-hexylamine modified 27-mer ODN with a sequence complementary to the initiation codon region of the mRNA transcript for the regulatory protein calmodulin in *Paramecium tetraurelia*.

The nucleophilic hexylamine linker groups were added at the 5'-terminus of the ODNs during automated synthesis using a commercially available phosphoramidite reagent. The 3'-hexanol modification in ODN2 was added at the 3'-terminus through use of a hexanol modified solid support.

The following model peptides were supplied by Multiple Peptide Systems (San Diego, Calif.) as the free sulfhydryl compounds (95+% pure):

PEP1: Sequence ID No.: 3 $H_2N$-cys-thr-pro-pro-lys-lys-lys-arg-lys-val-$CONH_2$ PEP2: Sequence ID No.: 4 $H_2N$-cys-asn-ser-ala-ala-phe-glu-asp-leu-arg-val-leu-ser-$CO_2H$ PEP3: Sequence ID No.: 5 $H_2N$-met-asn-lys-ile-pro-ile-lys-asp-leu-leu-asn-pro-gln-cys-$CONH_2$ These peptides were prepared using standard solid phase synthesis techniques and were purified by C18 HPLC. The purified peptides were carefully handled under argon to prevent oxidation to disulfides.

The chemistry illustrated in FIG. 3 was used for preparation of ODN-peptides. Conversion of the nucleophilic 5'-hexylamine group of the ODN to an electrophilic group (A) involved treatment with excess iodoacetic anhydride. Iodoacetic anhydride acts as a heterobifunctional linker in that it has two electrophilic sites of differing reactivity. The anhydride functional group reacts rapidly with the primary amino group whereas the iodoacetyl functional group is left untouched for further reaction with the peptide sulfhydryl in the next step.

Figure 5:
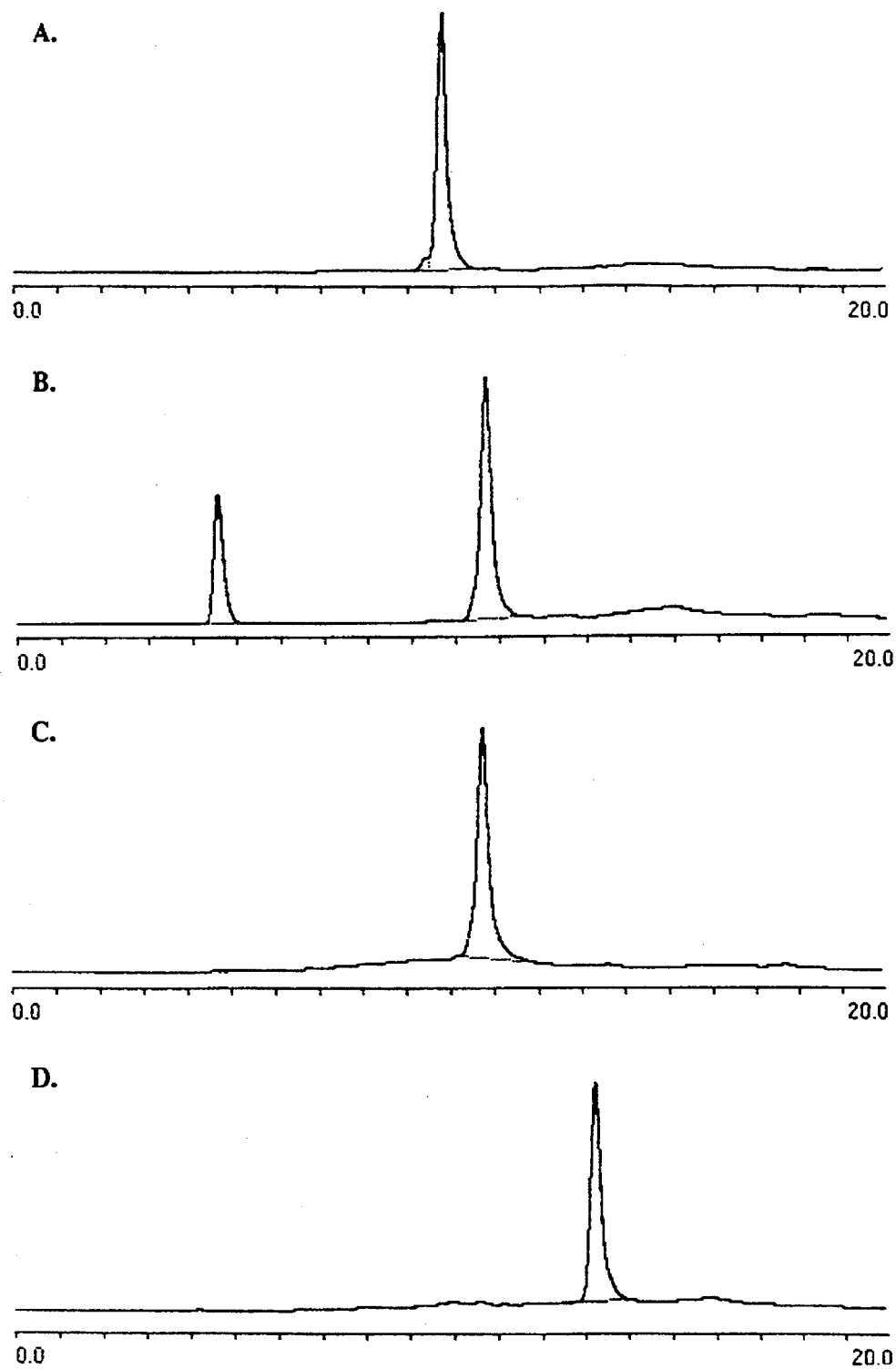
FIG. 5 shows C-18 HPLC chromatograms which illustrate the preparation and purity of the MODEL ODN-peptide conjugates.

Thus, treatment of hexylamine modified ODNs with 100 equivalents of iodoacetic anhydride at pH 8.3 as described in EXAMPLE I gives quantitative conversion to the desired iodoacetamide-ODN (IA-ODN). Since ODNs have strong UV absorbance at 260 nm, the course of the conjugation reaction was easily monitored by reverse phase (C-18) HPLC. As shown in FIG. 5 (Panels A and B) the starting hexylamine modified ODN (ODN2, 9.8 min peak) is completely converted to the desired iodoacetamide ODN (IA-ODN2, 10.7 min peak) in less than 60 min. Comparative experiments with three commercially available heterobifunctional linkers (sulfo-SIAB, SIAB, NHS-iodoacetate) showed that iodoacetic anhydride has many advantages over these prior art linkers. One advantage is that iodoacetic anhydride is much less expensive, another that it gives fewer side reactions. As far as the present inventors are aware, the use of iodoacetic anhydride for preparation of IA-ODNs, is novel, and so is the use of IA-ODNs for preparation of ODN conjugates.

Although they are stable in solution, the IA-ODNs are typical of electrophilic ODNs in that they do not survive lyophilization conditions. However, in accordance with the present invention ultrafiltration separation techniques (such as the system described below in EXAMPLE I) are excellent for purification of these reactive ODN derivatives. As shown in FIG. 5 (Panels B and C), through ultrafiltraton the purified IA-ODN2 (10.7 min peak) is completely separated from small molecular weight iodoacetyl contaminants (4.6 min). It is important that the aqueous solutions of IA-ODN are never taken to dryness.

Referring still primarily to FIG. 3, treatment of the iodoacetamide-ODNs with excess (for example 5-equivalents) of the desired sulfhydryl containing peptide gives quantitative conversion to the peptide-ODN conjugates. (For specifics see EXAMPLE II). However, C-18 HPLC analysis indicated different reaction kinetics for the three peptides (PEP1, PEP2 and PEP3) that correlated to the cationic nature of the peptides. Reaction with PEP1 (net charge=+5) was complete in minutes, whereas PEP2 (net charge=0) required 20 hr, and PEP3 (net charge=+1) required 3 hours.

The peptide-ODN conjugates can be readily purified by HPLC and lyophilized. In the specific examples, isolated yields of 98%, 97%, and 87% were obtained for each of the three peptide-ODN2 conjugates. The peptide-ODN conjugates showed one peak by C-18 HPLC and one band by polyacrylamide gel electrophoresis. FIG. 5 (Panel D) illustrates the purity of the conjugate of ODN2 and PEP3.

The ODN-peptide conjugates prepared from ODN1 were further characterized by thermal denaturation studies as described in EXAMPLE III. The dissociation of duplexes formed from equimolar concentrations of the ODN1-peptide conjugates and an unmodified 20-mer ODN target were examined. The changes in absorbance at 260 nm were measured as a function of temperature and the melting temperatures (Tm) were determined. The results indicate that the 5'-peptide modifications have little effect on the hybridization properties of the ODN. The results from these studies demonstrate that iodoacetamide-ODNs are cleanly prepared from hexylamine-ODNs in accordance with the present invention and that there are no competing side reactions (i.e. modification of the unprotected nucleotides) since these would have interfered with hybridization. These $T_m$ studies also demonstrate that even large fragments from a peptide linker have little effect on the hybridization properties (the sequence specific binding mechanism) of the larger molecular weight ODN drugs. Therefore, amino acid residue(s) from proteolysis of the linker are, generally speaking, expected to have little effect on the biological activity of the released ODN.

The results from the foregoing embodiments with model peptides demonstrate that iodoacetamide-ODNs react with the free sulfhydryl group on the cysteine residue of a peptide without significant competing side reactions with primary amines on the lysine residues. Especially striking were the results with PEP1. In accordance with the present invention, this lysine rich peptide reacted cleanly with the iodoacetamide modified ODN, thus clearly indicating that nucleophilic sulfhydryl groups react much faster with iodoacetamide-ODNs than do the primary amine groups in the lysine residues.

Thus, in accordance with the present invention ODN-peptides are prepared from heterobifunctional peptide groups wherein the peptide has a thiol group (B) which reacts much faster than a nucleophilic amine group (C). The residual nucleophilic "handle" (C) is utilized for crosslinking reactions to carriers or targeting ligands.

As noted earlier (FIG. 3), other chemical linker groups (A), (B) can be used to prepare ODN-peptide conjugates which bear, on the peptide, nucleophilic or electrophilic "handles" (C). In the above given example, the synthetic peptides included the amino acid cysteine as the thiol containing linker (B), and the amino acid lysine as the primary amine containing linker (C). Other suitable thiol or amine containing fragments can be substituted for these amino acids to provide a peptide suitable for conjugating the ODN with a lysosomotropic carrier. Such peptide linkers, bearing the appropriate amino acid protecting groups, can become readily apparent to those skilled in the art. In addition, different combinations of electrophilic and nucleophilic crosslinking groups can be used. In the above examples, electrophilic ODNs were coupled to nucleophilic peptides. Alternatively, one can use nucleophilic (thiol substituted) ODNs and react them with electrophilic peptides (i.e. iodoacetamide derivatives at the N-terminal amino groups, without departing from the scope of the invention.

The conjugation chemistry which is illustrated in FIG. 3 for the 5'-terminus of the ODN can also be performed at the 3'-terminus of the ODN. 3'-hexylamine modified ODNs are readily prepared from a specially modified solid support (Petrie, C. R., Reed, M. W., Adams, A. D., and Meyer, R. B., Jr. (1992), An improved CPG support for the Synthesis of 3'-amine-tailed oligonucleotides, *Bioconjugate Chem.* 3, 85). Addition of the peptide linker at the 3'-terminus may be advantageous in certain circumstances. For example, other conjugate groups can be readily added to the 5'-terminus of ODNs as the last step of automated synthesis. Conjugating the peptide linker to the 3'-terminus can help to prevent nuclease degradation.

Cleavable Peptide Linkers

Figure 6:
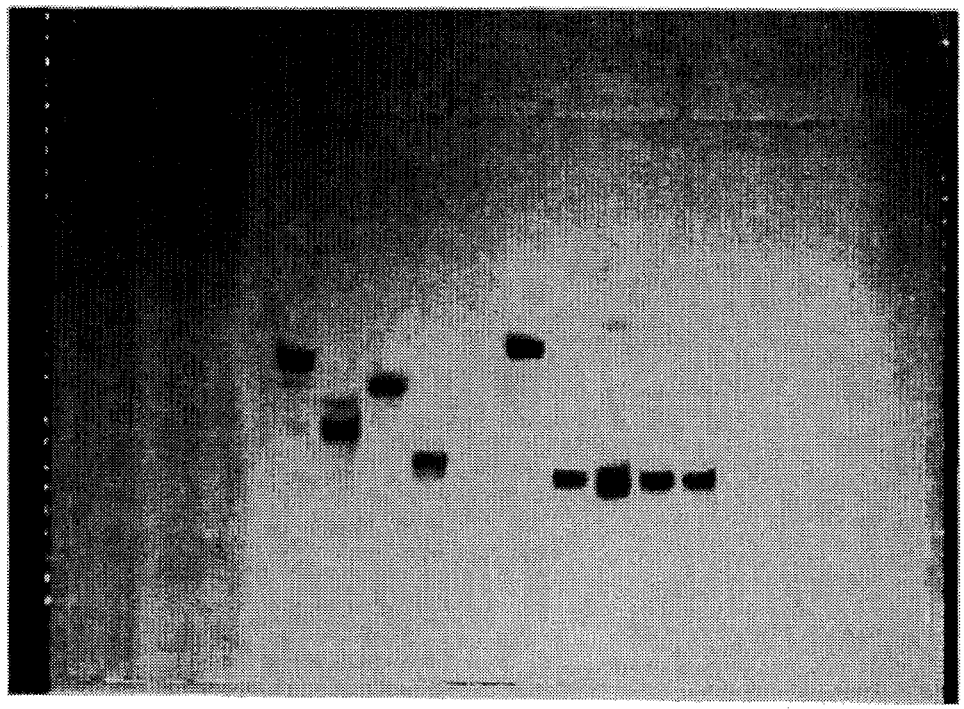
FIG. 6 is a photo of a polyacrylamide gel which illustrates that the peptide linking arms of MODEL ODN-peptide conjugates are cleaved by proteases (trypsin in this case).

The model ODN-peptide conjugates were further characterized by their susceptibility to proteolysis with trypsin. (For detail see EXAMPLE IV). As is known in the art, trypsin catalyzes the hydrolysis at the carboxyl side of lysine or arginine residues in the peptides. It was found in accordance with the present invention that trypsin had no effect on the ODN as shown by polyacrylamide gel electrophoresis in FIG. 6. This experiment shows the feasibility of using peptides as cleavable linkers in accordance with the present invention, wherein the peptide is cleaved by enzymes which do not degrade ODNs.

The choice of peptide sequence is critical to the success of the delivery system. For an effective "bioreversible" drug delivery system in accordance with the present invention, the ODN-targeting ligand linkage must be stable to serum proteases, yet cleaved by the lysosomal enzymes in the target cell. It has been shown in the prior art that the lysosomal thiol-proteinases, in particular cathepsin B, are the enzymes most important in cleavage of oligopeptide drug-polymer linkages. On the basis of studies done using rat liver lysosomal enzymes, the following two peptides were selected, which are expected to be also readily cleaved by proteases in human liver cells.

PEP4: Sequence ID No.: 6 $H_2N$-cys-leu-ala-leu-ala-lys-$CONH_2$

PEP5: Sequence ID No.: 7 $H_2N$-cys-gly-phe-leu-gly-lys-$CONH_2$

It is also within the scope of the present invention to isolate and identify specific proteases present in the lysosomes of targeted cells, and thereafter design specific cleavable peptide linkers for optimum release of ODN drug from the targeting ligand.

In the examplary PEP4 and PEP5 peptides the amino acids "leu-ala-leu-ala" Sequence ID No.: 13 and "gly-phe-leu-gly" Sequence ID No.: 2 respectively, comprise the "cleavable linkers". The cysteine residues have been added to the amino terminus of the peptides in accordance with the present invention to provide an attachment point for the iodoacetamide-ODN derivative. The lysine residue has been added in accordance with the invention to provide a primary amine containing modification for attachment to the desired lysosomotropic carrier. As is described above, iodoacetamide-ODNs are selectively attached in accordance with the invention to the cysteine residue of peptides containing lysine residues. Thus the "heterobifunctional" peptide linkers PEP4 and PEP5 are reacted in accordance with the invention, with IA-ODNs as shown in FIG. 3. The four internal amino acids in the peptide sequences PEP4 and PEP5 do not contain nucleophilic functional groups. This allows selective crosslinking of the primary amino group (C) of the ODN-peptide linker to a suitable functional group on the lysosomotropic carrier of choice.

In order to further illustrate the conjugation chemistry, an iodoacetamide derivative of an ODN-peptide was prepared using MODEL ODN3 and the cleavable, crosslinkable peptide PEP4.

ODN3: Sequence ID No.: 10 H$_2$N—(CH$_2$)$_6$—O—PO$_2^-$-
5'O—GTTCTCCATGTTCAG—O—PO—$_2$—O—
(CH$_2$)$_6$OH ODN3 is a 3'-hexanol, 5'-hexylamine modified 15-mer ODN with a sequence complementary to the initiation codon region of the mRNA transcript for the Hepatitis B surface antigen in HepG2 cells.

The 5'-hexylamine ODN was first converted to IA-ODN3 and then coupled to the free sulfhydryl form of PEP4 under the conditions described in EXAMPLE II. The terminal lysine residue of the peptide linker in ODN3-PEP4 was further converted to the corresponding iodoacetamide derivative as described in EXAMPLE XI. HPLC analysis indicated clean conversion of ODN3-PEP4 (elution time= 12.0 min) to IA-ODN3-PEP4 (elution time=15.0 min). This example provides an ODN derivative which can be further linked to a sulfhydryl modified carrier via a cleavable peptide linker arm.

Synthesis of ODN-Peptide-Surfactant Conjugates (Class 1)

Chemistry suitable in accordance with the present invention for synthesis of ODN-peptide-surfactant conjugates is illustrated in FIG. 4. The reactive primary amino group (C) on the ODN-peptide linker (FIG. 3) is first derivatized with iodoacetic anhydride to give reactive iodoacetamide derivatives as described above and in Example XI. The iodoacetamide derivative of the ODN-peptide conjugate is then reacted with thiol derivatized membrane anchor molecules. This efficient and versatile iodoacetamide/thiol coupling chemistry, as described for the peptide thiols (EXAMPLE II), can be used for the preparation of a wide variety of ODN-peptide-carriers.

Attachment of lipophilic groups to polyanionic ODNs give conjugates with surfactant properties by virtue of their "amphipathic" nature. For example, it is known that aqueous solutions of cholesterol modified ODNs form foams when shaken. Although the behavior of these "ODN-soaps" at cellular membrane surfaces is not well understood, it is believed that the lipophilic groups enhance affinity of ODNs for cells. A vast number of hydrophobic "membrane anchors" are known in the prior art to be suitable building blocks for surfactants, and can therefore be incorporated into the "ODN-peptide-carrier" molecules of the prevent invention.

Thus, ODN-soaps useful in accordance with the present invention are for formulation into ointments that aid in penetration of the ODN through skin tissue for topical applications. The lipophilic "anchor" inserts into the plasma membrane of a target cell, thus allowing cellular uptake by "fluid phase endocytosis". Upon reaching the lysosome, the peptide linker is degraded and the therapeutic ODN passes through the lysosomal membrane and into the cytosol. The therapeutic ODN can be further modified with groups that aid in transport through membranes.

Referring now to FIG. 7, a versatile method for preparation of thiol modified polymeric carriers is illustrated. The chemistry employed here is based on the efficient β-cyanoethyl phosphoramidite coupling chemistry that has been developed in the prior art for preparation of nucleic acid polymers. In the illustrated example, the polymeric carriers are synthesized on a hexanol modified solid support of the prior art using standard ODN synthesis conditions. Three types of novel phosphoramidite monomeric "anchor units" are shown in FIG. 7 which can be polymerized to provide "membrane anchors" with different lipophilic properties. Generally speaking, the monomers are polymerized in a stepwise fashion to give carriers of discrete sizes depending on the number of synthetic cycles. The surfactant carriers prepared from these monomers have the additional benefit of being water soluble by virtue of the hydrophilic phosphate residues which are interspersed throughout the polymers. This allows conjugation chemistry to be carried out under aqueous conditions. The linker chemistry that has been developed for preparation of ODN conjugates is easily applied to these machine-made carriers. As shown in FIG. 7, nucleophilic thiol linker groups can be attached to the polymeric carriers as a final step through use of a commercially available phosphoramidite reagent.

Specifically, one type of phosphoramidite monomer which is usable as a sufactant carrier in the present invention, and which is novel per se, is derived from hydroxyprolinol. The preparation of acridine and cholesterol derivatized hydroxyprolinol derivatives is described elsewhere (Reed, M. W., Adams, A. D., Nelson, J. S., and Meyer, R. B., Jr. (1991), Acridine and Cholesterol-Derivatized Solid Supports for Improved Synthesis of 3'-Modified Oligonucleotides., *Bioconjugate Chem.*, 2, 217). The contents of this reference is expressly incorporated herein. Enantiomerically pure hydroxyprolinol and certain derivatives are described in our application for U.S. Letters patent, Ser. No. 07/574, 348, filed on Aug. 28, 1990, which is also expressly incorporated herein. With reference to FIG. 7, aliphatic lipids (e.g. palmitic acid to give 1c), and other lipophilic groups can be introduced at the free amino group of hydroxyprolinol. (EXAMPLE V describes synthesis of the phosphoramidite monomer of the acridine containing hydroxyprolinol "anchor unit" 1a).

A second type of phosphoramidite monomers which can be polymerized to provide "membrane anchor" building blocks within the present invention and which are novel, are derivatives of alkanols, also shown in FIG. 7. These simple surfactant building blocks can be prepared with a variety of alkyl chain lengths. (EXAMPLE VI describes synthesis of the phosphoramidite monomer of the hexanol containing "anchor unit" 2.)

A third type of phosphoramidite monomers which can be polymerized to provide a "membrane anchor" building units of the ODN-peptide-carrier molecule of the present invention, and which are novel per se are derivatives of polyethylene glycols (PEG). These derivatives have unique properties which make them desirable for modification of biologically active molecules. These properties include: a wide range of solubilities, lack of toxicity, absence of antigenicity and immunogenicity, non-interference with enzymatic activities and conformations of polypeptides, nonbiodegradability, and ease of excretion from living organisms. These building blocks can be easily prepared with a variety of alkyl chain lengths. (EXAMPLE VII describes synthesis of the phosphoramidite monomer of the tetraethylene glycol containing "anchor unit" 3.)

The steps of synthesizing the polymer from the above-noted monomers are conducted in analogy with polymer synthesis known in the art, and are not described in detail. These steps are illustrated in FIG. 7. A nucleophilic SH group is introduced by using the appropriate thiol phosphoramidite. The SH group serves to couple the polymeric membrane anchor to the iodoacetamide derivatized ODN-peptide compound. Other types of conjugation chemistry can be substituted for the iodoacetamide/thiol chemistry shown in FIG. 4.

Synthesis of ODN-Peptide-Polyamine Conjugates (Class 2)

An example of the synthesis of ODN-peptide-polyamine conjugates is illustrated in FIG. 4. In accordance with this example, cyanuric chloride is used to couple the amino linker group (C) on the ODN-peptide to an amino group on the carrier (targeting ligand).

Specifically, ODN-linker-$NH_2$ groups are "activated" with cyanuric chloride to give stable, electrophilic derivatives that can be further reacted with amine containing polymers.

The ODN-polyamine coupling chemistry is illustrated using MODEL ODN4.

ODN4: Sequence ID No.: 11 $H_2N$—$(CH_2)_6$—O—$PO_2^-$-
5'O-CTGCTGCCTCCCGTAGGAGT ODN4 is a 5'-hexylamine modified 20-mer ODN which has been used in the prior art as a universal signal probe for hybridization assays.

Treatment of ODN4 with 100 equivalents of cyanuric chloride gives only the mono-ODN adduct, as described in detail in EXAMPLE VIII. Since the remaining two chlorines are "deactivated", cyanuric chloride acts as an inexpensive heterobifunctional linker for connecting two molecules via amino groups. The cyanuric chloride activated-ODNs (CC-ODNs) are stable in solution for weeks but (like most electrophilic ODNs) decompose upon lyophilization. The CC-ODNs are readily purified by ultrafiltration techniques. Although bis-adducts of amine-tailed ODNs with cyanuric chloride are not formed, CC-ODNs react rapidly with polyamines. Presumably this increase in reaction kinetics is controlled by electrostatic interactions of the macromolecules. No side reactions of cyanuric chloride with the heterocyclic bases can be detected.

Figure 8:
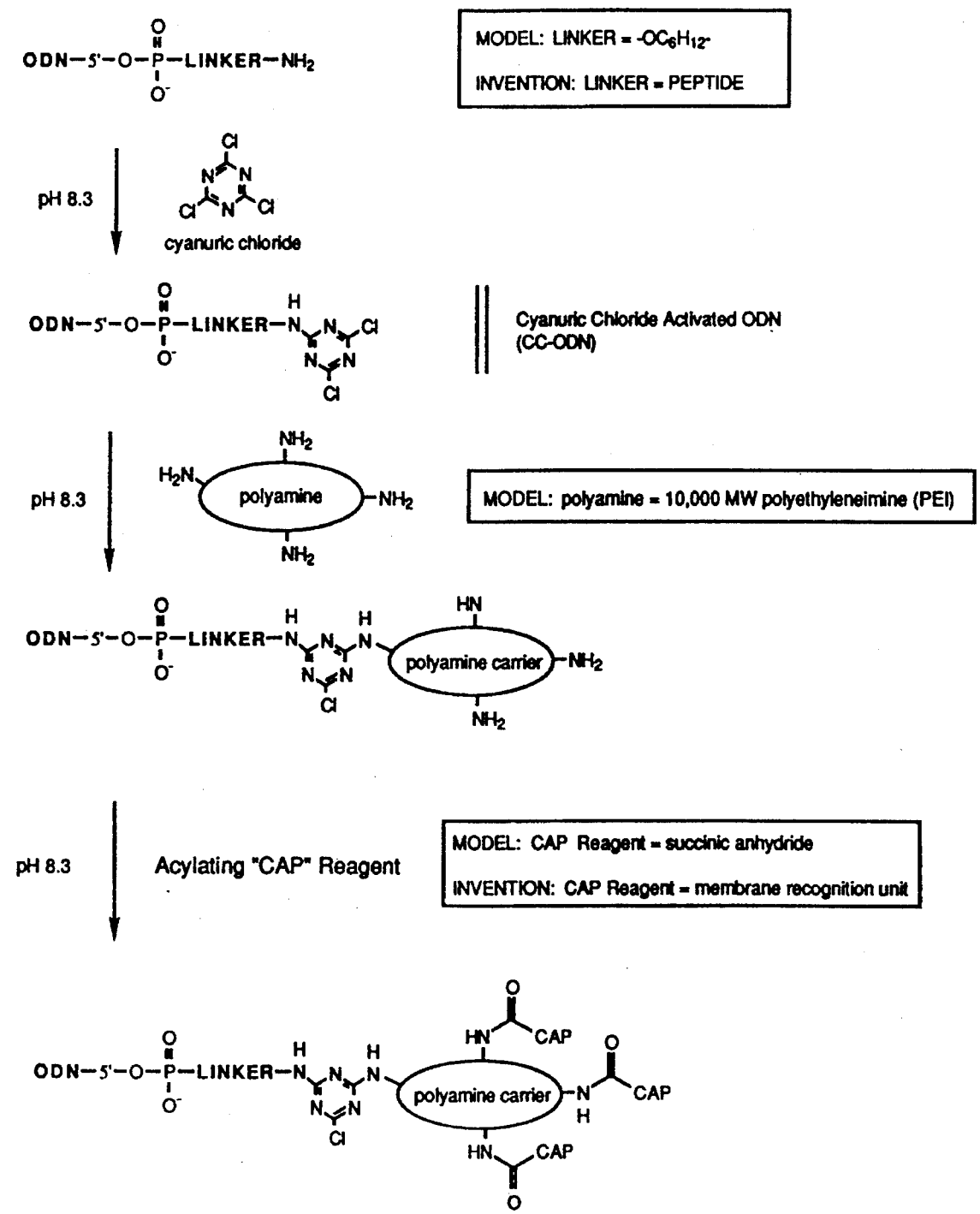
FIG. 8 illustrates a synthetic scheme used for preparation of ODN-linker-polyamine carrier conjugates.

The cyanuric chloride activated ODN (CC-ODN3) is further reacted with polyethyleneimine (10,000 MW polyethyleneimine (PEI), in the example), as described in detail in EXAMPLE IX. The ODN-PEI conjugate which can be isolated presumably exists as a heterogeneous mixture of products with various ratios of ODN:PEI. The material balance (90% recovered ODN after purification in the example) implies that the average number of ODNs per polyamine is approximately 5. After formation of the ODN-polyamine conjugate, residual cationic charges on the PEI are preferably "capped" by treatment with succinic anhydride. This procedure prevents "non-specific adsorption" of non-target nucleic acids by the PEI. The "capping" reaction also serves as a model for introduction of "membrane recognition elements", as illustrated in FIG. 8. "Capping" of polyamine carrier molecules with succinic anhydride is an optional step that, in accordance with the invention, allows the "stickiness" of the ODN conjugates to be modulated. The net charge on the ODN-peptide-polyamine conjugates can also be controlled by varying the size of the polyamine.

A variety of polyamines have been shown in the prior art to improve uptake of macromolecules into cells. In FIG. 9 the structures of three polyamines are shown which are preferred in the present invention. 1:1 conjugates of ODN-peptides with polyamines of average MW 10,000 are contemplated in accordance with the present invention to be most useful as ODN delivery vehicles. It is contemplated that for efficient drug delivery the polyamine must contain enough cationic residues (at physiologic pH) to neutralize the anionic charges on the ODN and also provide a net positive charge to the complex.

Referring specifically to FIG. 9 the "polyamines" preferably used in this aspect of the invention are illustrated.

Polyethyleneimine (PEI) is an inexpensive, commercially available polymer which is available in a variety of average molecular weight ranges (600, 1200, 1800, 10,000 and 70,000). PEI polymers are very highly branched into a "bush-like" structure. A 10,000 MW polymer of PEI contains approximately 58 primary amines, 116 secondary amines, and 58 tertiary amines.

Poly-L-lysine (PLL) is available as the hydrobromide salts from Sigma Chemical in a variety of average molecular weight ranges. The polymers are prepared by base-initiated polymerization of the corresponding N-carboxyanhydride. The MW range of most interest to this invention are 4K–15K, 15K–30K, and 30K–70K. A 10,000 MW polymer of PLL contains approximately 47 primary amines, and is much less densely charged than PEI. The naturally occurring poly-L-backbone can be degraded by lysosomal enzymes, but this carrier may pose toxicity problems. The "non-natural" poly-D-isomers are also commercially available and can be used as control compounds to study non-degradable carriers.

A unique class of quasi-spherical, amine coated polymers has recently become commercially available (Polysciences Inc., Warrington, Pa.). Dendrimers are prepared in the desired size through a series of well defined organic reactions known in the art. The repeating amide units of these polymers are added in discrete layers or "generations". Each additional layer gives a larger polymer with a discrete molecular weight and a specified number of surface amino groups. The larger dendrimers (>4th generation) have a distinctly spherical shape. A fifth generation dendrimer has a molecular weight of 10,632 and contains 48 terminal primary amines. Roberts, J. C., Adams, Y. E., Tomalia, D., Mercer-Smith, J. A., and Lavallee, D. K. (1990), Using starburst dendrimers as linker molecules to radiolabel antibodies, *Bioconjugate Chemistry*, 1, 305. Dendrimers are contemplated to be well suited for applications as carriers in ODN delivery systems. The commercially available dendrimers come in a variety of sizes and have good water solubility. The discrete molecular weight of these amine coated polymers (polydispersity=1.00) allows preparation and isolation of ODN-peptide-dendrimer conjugates of high purity.

Synthesis of ODN-Peptide-Ligand Conjugates (Class 3, Method A)

Two methods suitable for synthesis of ODN-peptide-ligand conjugates are illustrated in FIG. 4. The indirect method (Method A) where residual amino groups on the ODN-peptide-polyamine conjugates (Class 2) are reacted ("capped") with suitable membrane recognition elements. As described earlier, hepatocytes have a membrane bound receptor which recognizes galactose containing ligands. Likewise, macrophages recognize mannose containing ligands. FIG. 10 shows the structure of carbohydrate containing molecules which can be used as reagents ("CAP reagents") to attach membrane recognition elements to amine containing carriers.

Thus, the peracetylated, carbohydrate containing, tetrafluorophenyl (TFP) esters 4a and 4b shown on FIG. 10 are constructed from known carboxylic acid precursors for example as described in EXAMPLE X. P-nitrophenyl ester derivatives of these same carbohydrates are used in the prior art for preparation of the more complex "cluster ligands" (Ponpimom, M. M., Bugianesi, R. L., Robbins, J. C., Doebber, T. W., and Shen, T. Y. (1981), Cell-specific ligands for selective drug delivery to tissues and organs, *J. Med. Chem.* 24, 1388). The derivatives 4 can be used as acylating CAP Reagents for the construction of ODN-peptide-ligand conjugates as illustrated in FIG. 8. In accordance with the present invention each polyamine carrier is "capped" with many carbohydrate ligands, thus providing the multivalency that is required for efficient binding of ligands by the carbohydrate specific receptor.

The reaction ("capping") of ODN-peptide-polyamine carriers using the TFP esters 4 is analogous to the succinylation conditions provided in EXAMPLE IX. TFP esters react rapidly with amine modified ODNs under the described reaction conditions. It was found in accordance with the present invention that even with >100 equivalents of TFP ester, the heterocyclic bases in the ODN are not modified (as evidenced by thermal denaturation studies). In addition, the acetyl protecting groups on the carbohydrate rapidly hydrolyze at pH 8.3 to give, in the final product the desired hydroxyl form of the carbohydrate membrane recognition elements.

The use of ODN-peptide-dendrimer conjugates allows the topology of the membrane recognition elements to be controlled. The distance between the amine containing tips on the "arms" of the dendrimers depend on the generation. "Capping" with the TFP esters (4) therefore provides sugar residues with specific geometric constraints. It is contemplated within the present invention to vary the size of the dendrimer to optimize binding to the sugar specific receptor.

The ODN-peptide-polyamine conjugates can also be conjugated to fully constructed targeting ligands. Since these ligands are generally macromolecular in nature, a single ligand may be suitable for the delivery of a number of therapeutic ODNs. Chemistry for attaching poly-L-lysine to targeting proteins is known.

Synthesis of ODN-Peptide-Ligand Conjugates (Class 3, Method B)

A direct method for synthesis of ODN-peptide-ligand conjugates (Method A) is also illustrated in FIG. 4. Iodoacetamide/thiol coupling chemistry is preferred since it has been discovered in accordance with the present invention that iodoacetamide-linker-ODNs react with a variety of different thiol containing compounds. The ODN-peptide-$NH_2$ is first "activated" with iodoacetic anhydride, (for example as described in EXAMPLE XI) and thereafter conjugated to thiol containing targeting ligands as described in EXAMPLE II.

The just-noted direct conjugation of ODN-peptides to fully constructed targeting ligands (Method B on FIG. 4) is advantageous in that ligands with well understood targeting properties can be used. Targeting properties of the ligand are not affected significantly, if the ODN is attached to a functional group on the targeting ligand which is distinct from the receptor binding region of the ligand.

Especially illustrative as thiol containing targeting ligands, and preferred within the present invention are monoclonal antibodies, or fragments thereof. Free thiol groups on immunoglobulins (Ig) can be generated in accordance with the prior art by two different methods. Reductive cleavage of the native disulfides in the hinge region of the Ig can be achieved by mild treatment with reducing agents such as dithiothreitol (DTT). This method is also useful for generation of free thiols in antibody fragments such as F(ab')$_2$ or Fab. Reduced Fab from rabbit contains one thiol per targeting molecule. Fab from other animal sources contain one to three thiols. Alternatively, free thiols can be introduced into Ig by treatment with S-acetylmercaptosuccinic anhydride, 2-iminothiolane, N-succinimidyl 3-(2-pyridyldithio)propionate (SPDP), or other reagents that react with the ε-amino groups in native lysine residues.

An example of a fully constructed targeting ligand which is preferred for delivery of anti-hepatitis ODNs is asialoorosomucoid (ASOR). ASOR can be prepared from the blood plasma glycoprotein, orosomucoid, by treatment with neuraminidase, in accordance with prior art. As noted above, asialoglycoproteins such as ASOR are rapidly removed from the blood plasma of mammals by a carbohydrate recognition system present only in hepatocytes. It is known that a conjugate of the ASOR ligand with horseradish peroxidase is rapidly internalized in rat liver. Thiol modified ASOR has been prepared in the prior art, using SPDP, and was used for coupling to PLL. In accordance with the present invention, ODN-peptide-iodoacetamides are directly coupled to thiol modified ASOR to give ODN-Peptide-ASOR conjugates using the iodoacetamide/thiol coupling chemistry, as described for the peptide thiols (EXAMPLE II).

Another type of fully constructed targeting ligand are the polymers illustrated in FIG. 10. Monomers which contain suitable "membrane recognition elements" such as the CAP molecules of FIG. 10 are prepared from the CAP Reagents and amine containing monomer. For example, polymeric targeting ligands containing peptide backbones can be prepared from suitably functionalized lysine monomers by reacting the lysine monomer with the CAP reagents. Polymerization of the thus derivatized amino acid monomers is carried out using solid support based peptide synthesis conditions.

Modified nucleic acid monomers (phosphoramidites) are constructed from the CAP Reagents. An illustrative example is given in FIG. 10, wherein 5-methylamino-2'-deoxyuridine phosphoramidite has been reacted with a CAP reagent, and thereafter polymerized by using standard DNA synthesis conditions to give targeting ligands with phosphate-sugar backbones. As described above, thiol linker groups can be readily added at the terminus of the constructed polymers.

Another type of polymeric targeting ligand is synthesized from substituted hydroxyprolinol phosphoramidite monomers as illustrated in FIG. 10. This chemistry is directly analogous to that described above. For example, the carbohydrate containing TFP ester (4a or 4b) is reacted with hydroxyprolinol and further functionalized using standard conditions to give monomers which carry the carbohydrate moiety of formula 4a or 4b. The carbohydrate containing monomers are then polymerized to a desired size using standard ODN synthesis conditions, and a terminal thiol group is added as shown in FIG. 7. The resulting thiol modified carbohydrate polymer is directly coupled to ODN-peptide-iodoacetamides using the coupling conditions described in EXAMPLE II. A targeting ligand prepared from monomer 1 (of FIG. 7) wherein the CAP group is the α-D-mannose derivative derived from 4b is expected to be especially effective at targeting macrophages, since it is recognized by the polyanion receptor as well as the mannose receptor.

Therapeutic ODN-Targeting Ligand, "Matched Sets"

As described earlier, another aspect of the invention is a method to improve the potency of sequence specific ODN drugs by targeting them to specific tissue types. Many diseases are caused by excess production of proteins which elicit effects which are deleterious to the survival of the affected organism. Therapeutic ODNs can be designed which specifically inhibit production of these "deleterious" proteins within a normally healthy cell. Diseases generally are localized in certain topological areas or in certain types of tissue within an organism. It is desirable to match the therapeutic ODN with an ODN carrier system that concentrates the drug in the affected cells. Thus, "matched sets" of nucleic acid specific ODNs and tissue specific targeting ligands or carriers provide drugs with higher therapeutic index than traditional pharmaceuticals.

Specifically, deleterious proteins can be produced as a result of infection by pathogenic organisms such as viruses, bacteria, fungus or eukaryotic parasites. Harmful proteins need not be xenobiotic in origin. For example, the expression of oncogenes has been linked to cancer. Even proteins which are required for the health of an organism can be overproduced and cause toxic effects. For example, the proteins IL-1β and TNF-α are secreted by macrophages to elicit an inflammatory response in an organism. If these biological response modifiers (BRMs) are overproduced, then effects which are toxic to the organism can result (e.g. septic shock).

Topical application can be an especially effective route of administration for many types of diseased tissue. For example, sexually transmitted diseases such as human papilloma virus or herpes simplex virus commonly infect membranous tissue and cause eruptions in the skin of the genitalia. Herpes zoster is commonly localized at the basal ganglia of the thorax of infected individuals and causes the visible lesions on the skin known as "shingles". Herpes viruses can also be localized in the eye. As discussed above, Class 1 ODN-peptide conjugates (ODN soaps) can be especially useful for therapy of viral diseases such as these which are accessible by direct topical applications.

Systemic administration of ODNs presents a more complex delivery problem. The Class 3 ODN-peptide-targeting ligand conjugates of the invention are contemplated to be especially useful for delivery of therapeutic drugs to affected tissues which cannot be easily reached through non-invasive methods. As described earlier, these conjugates can be designed to recognize and bind to specific receptors on specific types of cells. An examplary "matched set" in accordance with the present invention is for therapy of Hepatitis B virus.

Listed below are several diseases which may be treated by systemic administration of "matched sets" of antisense ODNs and targeting ligand conjugates of this invention. The examples of antisense ODNs have either been reported (without the peptide and target ligand moieties) in cell culture models, or have been examined by the inventors. The ODN-peptide-ligand combinations of the invention are expected to give improved molar potency of ODNs in cell culture in comparison to unconjugated ODNs.

Hepatitis B. Antisense ODNs complementary to the translation initiation codon region of the HBsAg mRNA have been found to inhibit expression of secreted surface antigen. Conjugation of antisense ODNs to galactose coated polymers, with a cleavable peptide is expected to efficiently deliver the antisense ODN into the cytosol of hepatocytes and provide improved protein inhibition.

Leishmaniasis. The single celled protozoan Leishmania is a pathogenic human parasite. The amastigote form of the parasite takes refuge in the lysosomes of infected macrophages. The antisense ODNs complementary to the spliced leader sequence of the mRNAs in Leishmania can inhibit growth of this microorganism. Conjugation of antisense ODNs to mannose coated polymers with a cleavable peptide is expected to improve the sequence specific potency of this class of cytotoxic agent.

Septic Shock. As described above, production of the cytokines TNF-α and IL-1β by human macrophages drive the inflammatory response. Diseases as diverse as septic shock, arthritis, diabetes, and multiple sclerosis may be treatable by blockers of IL-1. Antisense ODNs to IL-1 and TNF-α have been reported. Conjugation of the appropriate antisense ODNs to mannose coated polymers with a cleavable peptide is expected to reduce production of these powerful BRMs.

AIDS. Human immunodeficiency virus type 1 (HIV-1) has been clearly identified as the primary cause of the acquired immunodeficiency syndrome (AIDS). The human T-cell lymphocyte is a major cellular target for the HIV virion. Antisense ODNs complementary to the viral RNA have been shown to inhibit HIV replication and expression in cultured T-cells. Conjugation of similar antisense ODNs to T-cell specific antibodies or antibody fragments is expected to improve the potency of these antiviral agents.

The activity of the therapeutic ODN-cleavable peptide-carrier molecules of the present invention can be confirmed in the following assays and test procedures.

Proteolysis Assay

Treatment of ODN-peptide-carrier conjugates with proteases releases the ODN from the carrier. These assays can be performed according to the protocol described in EXAMPLE IV.

Stability and Uptake Assay

The ability of the targeting ligands to facilitate uptake and release of ODNs into the cytosol is evaluated in a cell culture system. Thus, Hep G2 cultures are used to evaluate the uptake, the intracellular distribution and the stability of the ODN conjugates. By way of background, the uptake of asialoglycoproteins into this continuous cell line are well characterized. For the assay, the ODNs are internally labeled with $^{32}P$. To accomplish this, each ODN is synthesized in two component halves. The 5' half of the ODN is kinased in the presence of $^{32}P$-ATP and then ligated to the 3' half of the same ODN in the presence of a short complementary template ODN. The resultant internally radiolabeled ODN is isolated from its complement by denaturing and conjugated to cleavable peptide and carrier in the presence of cold carrier ODN.

For the uptake and stability studies, the radiolabeled ODN conjugates are added to the Hep G2 cultures at μM concentrations. At specified times the cells are washed and harvested. The resultant whole cell pellets are resuspended and vortexed in a standard lysis buffer containing 0.5% NP-40 nonionic detergent. The nuclei are washed once with the same buffer, and this wash buffer is combined with the original lysis solution. The cytoplasmic and nuclear fractions are each divided into two aliquots. One is resuspended in scintillant and counted, while the other is treated with proteinase K in the presence of EDTA and SDS and the nucleic acid alcohol precipitated in the presence of carrier. The purified nucleic acid is electrophoresed through a denaturing 20% polyacrylamide gel to determine the integrity of the ODN.

The relative distribution of counts between cytoplasmic and nuclear fractions provides an approximate indication of how much ODN has been released into the cytosol, since once this happens the ODN rapidly accumulates within the nucleus. The distribution of counts on the gel provides further indication of the state of the ODN. Rapidly moving, nonresolved products indicate nuclease digestion. Conversely, counts held up in the well reflect ODN still conjugated to the macromolecular carrier.

Antisense Assay for Hepatocyte Specific Carriers

ODN-peptide-carrier conjugates of the invention are preferably assayed for both uptake characteristics and antisense activity in a hepatoma cell line which supports the constitutive replication of hepatitis B virus (HBV).

The antisense ODN screen uses a Hep G2 cell clone in which a dimeric copy of the HBV genome has been stably integrated into the chromosomal DNA. The resultant 2.2.15 human hepatoblastoma cell line secretes both free hepatitis B surface antigen (HBsAg) and intact virions (i.e., Dane particles). In the assay, ODNs complementary to the translation initiation site in HBsAg mRNA are tested for their ability to inhibit synthesis (and hence) secretion of HBsAg into the culture medium.

The assay employs a convenient enzyme immunoassay kit available from Abbott to detect the secreted HBsAg. A typical assay is conducted in a microtiter plate employing triplicates of each sample. Generally, a concentration series of each antisense ODN is tested against a nonsense ODN with identical base composition and modification. The cells are washed prior to addition of the ODN in fresh medium and incubation is continued until the extracellular level of HBsAg is high; this can take several days, in which case multiple additions of the ODN can be made. At the conclusion of the assay, the medium from each well is removed and assayed for HBsAg level using the Abbott kit.

The Hep G2 cells are treated with various concentrations of the ODN-peptide-carrier conjugates, and the amount of secreted HBsAg is determined. The corresponding unconjugated antisense ODNs will serve as baseline controls. Potency is determined by serial dilution of an ODN stock solution by evaluating the concentration at which the detected HBsAg level is reduced by ½ (the inhibitory dose (50%), or $ID_{50}$).

Paramecium Antisense Assay. It is desirable that the 3'-modified antisense ODNs which are released from the macromolecular carrier molecule are still substrates for RNase H. Such modifications are evaluated by microinjection into Paramecium and monitoring their swimming behavior as described in Hinrichsen, R. D., Fraga, D. and Reed, M. W. (1992) 3'-Modified Antisense Oligodeoxyribonucleotides Complementary To Calmodulin mRNA Alter Behavorial Responses In Paramecium, *Proc. Natl. Acad. Sci., U.S.A.*, 89, 8601, which is expressly incorporated herein by reference. This assay is advantageous since microinjection allows intracellular mechanisms of action of modified antisense ODNs to be evaluated separately from membrane transport issues. Potency is determined by serial dilution of an ODN stock solution and evaluating the minimum effective concentration.

Methods of Administration; Formulations

The therapeutic ODN-cleavable peptide carrier formulations of the present invention may be administered topically, or systemically depending on the nature of the condition treated. The vehicles of administration, such as lotions, ointments, solutions, injections, tablets, capsules, etc. per se are well known in the art and need not be described here in detail.

SPECIFIC EXAMPLES

Physical properties of the modified oligonucleotides described in the following EXAMPLES are presented in Table I.

General Synthesis of 5'-Hexylamine Modified Oligodeoxynucleotides. 5'-Hexylamine modified oligonucleotides with the sequences 5'-CTCCATCTTCGTCACA (ODN1 Sequence ID No.: 8), 5'-TAATTATTCAGCCATTTAT-TATTAGTT (ODN2 Sequence ID No.: 9), GTTCTCCAT-GTTCAG (ODN3 Sequence ID No.: 10), and 5'-CTGCT-GCCTCCCGTAGGAGT (ODN4 Sequence ID No.: 11) were prepared on either a Milligen 7500 or an Applied Biosystems Model 380B using the protocols supplied by the manufacturer. Protected β-cyanoethyl phosphoramidites, CPG supports, deblocking solutions, cap reagents, oxidizing solutions, and tetrazole solutions were purchased from either Milligen or Glen Research. 5'-aminohexyl modifications were introduced using an N-MMT-hexanolamine phosphoramidite linker (Milligen). The 3'-hexanol modification was introduced into ODN2 and ODN3 through use of a hexanol modified CPG solid support which is made in accordance with the procedure of Hinrichsen, R. D., Fraga, D. and Reed, M. W. (1992) 3'-Modified Antisense Oligodeoxyribonucleotides Complementary To Calmodulin mRNA Alter Behavorial Responses In Paramecium, *Proc. Natl. Acad. Sci., U.S.A.*, 89, 8601. Analytical and preparative HPLC were carried out using a Rainin pump system equipped with a Gilson 116 UV detector. Pump control and data processing were performed using a Rainin Dynamax chromatographic software package on a Macintosh computer. After ammonia deprotection, the tritylated ODNs were HPLC purified by direct injection of the ammonia solution onto a Hamilton PRP-1 column (305×7.0 mm), and the product was eluted using a linear gradient of 20%–45% acetonitrile in 0.1M TEAA (pH 7.5) over 20 min (flow rate=4 mL/min). Appropriate fractions were combined and concentrated to dryness on a Savant Speed-Vac. The residue was detritylated in 80% acetic acid (500 μL, 28@C, 70 min), precipitated with 100 μL of 3M sodium acetate and 4 mL of 1-butanol, centrifuged, washed with 1 mL of ethanol, centrifuged, evaporated to dryness, and reconstituted with 1 mL of sterile distilled water.

Characterization of Modified ODNs. The concentrations of modified ODNs were determined from the UV absorbance at 260 nm. All ODN concentrations were measured in pH 7.2 PBS (9.2 mM disodium phosphate, 0.8 mM monosodium phosphate, 0.131M sodium chloride). An extinction coefficient for each ODN was determined using a nearest neighbor model substantially as taught by Cantor, C. R., Warshaw, M. M., and Shapiro, H. (1970), Oligonucleotide interactions. III. circular dichroism studies of the conformation of deoxyoligonucleotides, *Biopolymers* 9, 1059, correcting for the molecular weight of appended modifications. The value for ε was used to calculate a theoretical ratio of $A_{260}$ to concentration in μg/mL. The calculated concentration values (μg/mL) for $A_{260}$=1 OD unit are listed in Table I for all modified ODNs. The purified ODNs were analyzed by HPLC on a Dynamax C-18 column (0.75×25 cm) using a linear gradient of 5%–45% acetonitrile in TEAA over 20 minutes (flow rate=1 mL/min). ODN purity was confirmed by polyacrylamide gel electrophoresis (PAGE). The 5'-hexylamine modified ODNs (ODN1, ODN2, and ODN3) showed one peak by HPLC and one band.

EXAMPLE I

Synthesis of Iodoacetamide-ODNs (IA-ODN2). An aqueous solution of the 5'-hexylamine modified oligonucleotide, ODN2 (0.50 mL, 1.41 mg, 0.184 μmoles), was combined with 0.50 mL of 1.0M sodium borate buffer (pH 8.3) in a polypropylene eppendorf tube. Iodoacetic anhydride was added as a 50 mg/mL stock solution in acetonitrile (128 μL, 6.4 mg, 18 μmoles), and the heterogeneous mixture was vortexed for 1 h. C-18 HPLC analysis indicated complete conversion of ODN2 (9.8 min peak) to iodoacetamide-ODN2 (10.7 min peak) as shown in FIG. 5 (panels A and B). Excess iodoacetic anhydride and iodoacetate appears at 4.6 min. The crude reaction mixture was transferred to a 3,000 MW cutoff microconcentrator (Amicon) with 1.0 mL of 0.1M borate buffer (pH 8.3), and centrifuged to a retentate volume of $^{18}$0.1 mL. The retentate was reconstituted to 2 mL and the mix was re-concentrated. This process was repeated, and the retentate was reconstituted to 1.0 mL with 0.1M borate. As shown in FIG. 5 (panel C) this ultrafiltration process cleanly separated the iodoacetamide-ODN from the small molecular weight contaminants. The UV absorbance at 260 nm indicated a concentration of 1.18 mg. This corresponds to an isolated yield of 82%. The IA-ODN solution was stored at −20° C. HPLC analysis after 1 year showed less than 10% decomposition.

A similar procedure was used for preparation of IA-ODN1. The synthetic results are presented in Table I.

EXAMPLE II

Synthesis of ODN-Peptide Conjugates (ODN2-PEP2). A solution of 294 μg (37.5 nmoles) of iodoacetamide-ODN2 in 0.1M sodium borate buffer (pH 8.3) was transferred to a 1.1 mL septum capped glass vial and degassed by sparging with argon for 10 min. A 1.0 mg/mL stock solution of the thiol containing peptide (PEP2) in degassed water was prepared. 267 μL (188 nmoles) of the PEP2 solution was added to the solution of IA-ODN2, the mixture was degassed and kept under an argon atmosphere for 23 h. C18 HPLC analysis indicated complete conversion of IA-ODN2 (10.7 min peak) to ODN2-PEP2 (13.2 min peak). The reaction mixture was concentrated to dryness on a Speed-Vac and reconstituted with 100 μL of TEAA buffer. The mixture was purified by C-18 HPLC using the column and gradient described in FIG. 5. The peak corresponding to product was collected in one fraction and dried on a Speed-Vac. The solid residue was reconstituted with 200 μL of water, and the purified product (ODN2-PEP2) was analyzed by C-18 HPLC (FIG. 5, Panel D). The concentration was determined by $A_{260}$ to be 1.67 mg/mL (97% recovery).

A similar procedure was used for preparation of ODN1-PEP1, ODN1-PEP2, ODN1-PEP3, ODN2-PEP1, ODN2-PEP3 and ODN3-PEP4. The ODN-peptide conjugation reactions were conveniently followed by C18 HPLC. PEP1 reacted completely in <1 h, PEP2 required 20 h, and PEP3 required 3 h. The synthetic results are presented in Table I.

The sequences of the peptides are as follows:

PEP1 Sequence ID No.: 3 H$_2$N-cys-thr-pro-pro-lys-lys-lys-arg-lys-val-CONH$_2$

PEP2 Sequence ID No.: 4 H$_2$N-cys-asn-ser-ala-ala-phe-glu-asp-leu-arg-val-leu-ser-CO$_2$H.

PEP3 Sequence ID No.: 5 H$_2$N-met-asn-lys-ile-pro-ile-lys-asp-leu-leu-asn-pro-gln-cys-CONH$_2$ PEP4 Sequence ID No.: 6 H$_2$N-cys-leu-ala-leu-ala-lys-CONH$_2$

EXAMPLE III

Thermal Denaturation Studies (ODN1-Peptides). Thermal dissociation curves were obtained by following changes in $A_{260}$ of aqueous solutions containing equimolar amounts of the particular ODN1-peptide described above and an unmodified 20-mer ODN complement with the base sequence 5'-GTGACGAACATGGAGAACAT Sequence ID No.: 14. The 5'-hexylamine modified 16-mer (ODN1) was used as a control in each run. ODNs were prepared as 2 μM solutions in pH 7.2 PBS. A Gilford System 2600 UV-VIS spectrophotometer equipped with a Gilford 2527 Thermoprogrammer was used. The samples were heated from 15° C. to 85° C. with a temperature increase of 0.5° C./min. Absorbance vs. time and the first derivative data were recorded automatically. The $T_m$ curves were typical of those obtained with unmodified ODNs. The $T_m$ was determined using the derivative maxima: ODN1, $T_m$=62.8° C.; ODN1-PEP1, $T_m$=61.8° C.; ODN1-PEP2, $T_m$=59.0° C.; ODN1-PEP1, $T_m$=60.8° C.

EXAMPLE IV

Protease Degradation Studies (ODN1-Peptides). The three ODN1-peptide conjugates (described in Table I) were characterized by treatment with trypsin. Solutions of 2 μg of the ODN-peptide in 7 μL of water were combined with 1 μL of 10x trypsin disruption solution, 1 μL of 100 mM Tris buffer (pH 9.0), and 1 μL of 100 mM EDTA. After digesting 60 min, the samples were loaded on 20% denaturing polyacrylamide gel. Electrophoresis indicated complete proteolysis of starting ODN1-peptide (see FIG. 6, lanes 1–6). Trypsin had no effect on an unmodified ODN1 control (lanes 8 and 9).

EXAMPLE V

Synthesis of Substituted Hydroxyprolinol Phosporamidites (1-[5-(9-Acridinyl)-1-oxopentyl]-5-[bis(4-methoxyphenyl)phenylmethoxy]methyl-(3R-trans)-O-[(N,N-diisopropylamino)-β-cyanoethoxy-phosphino]-pyrrolidinol (1a)). The acridine substituted precursor alcohol to the phosphoramidite (1a) was prepared according to the literature procedure (Reed, M. W., et al. Acridine and Cholesterol-Derivatized Solid Supports For Improved Synthesis of 3'-Modified Oligonucleotides, Bioconjugate Chem., 2, 217). To a solution of 203 mg (0.30 mmol) of the alcohol in 15 mL of methylene chloride was added 0.25 mL (1.4 mmol) of anhydrous N,N-diisopropylethylamine. While stirring under argon, 2-cyanoethoxy-N,N'-diisopropylaminochlorophosphine (0.13 mL, 0.66 mmol) was added via syringe. After 1 h, the solution was stripped of solvent and the residual yellow syrup was taken up in ~0.5 mL methylene chloride. This solution was purified by flash chromatography (2×36 cm silica) using a gradient of ethyl acetate in hexanes (10% triethylamine). The product eluted with 4.5:4.5:1, ethyl acetate-hexanes-triethylamine. Removal of solvents gave 229 mg (87% yield) of the phosphoramidite (1a) as an off-white solid foam: TLC (4.5:4.5:1 ethyl acetate-hexanes-triethylamine) $R_f$=0.34, yellow spot with blue fluorescence which stained orange upon spraying with 10% sulfuric acid in methanol.

EXAMPLE VI

Synthesis of Alkanol Phosphoramidites (1-O-(4,4'-dimethoxytrityl)-6-O-[N,N-diisopropylamino)-β-cyanoethoxy-phosphino]-1,6-hexanediol (2)).

The precursor alcohol to the phosphoramidite (2) was prepared according to the literature procedure (Hinrichsen, R. D., Fraga, D. and Reed, M. W. (1992) 3'-Modified Antisense Oligodeoxyribonucleotides Complementary To Calmodulin mRNA Alter Behavorial Responses In Paramecium, *Proc. Natl. Acad. Sci., U.S.A.*, 89, 8601). To a solution of 0.70 g (1.66 mmol) of the alcohol in 85 mL of methylene chloride was added 1.4 mL (8.0 mmol) of anhydrous N,N-diisopropylethylamine. While stirring under argon, 2-cyanoethoxy-N,N'-diisopropylaminochlorophosphine (0.70 mL, 2.9 mmol) was added via syringe. After 0.5 h, the solution was quenched with 0.6 mL of methanol and poured into 250 mL of ethylacetate (10% triethylamine). The organic layer was washed with 2×200 mL of saturated sodium bicarbonate, 2×200 mL of saturated sodium chloride, and dried over sodium sulfate. The solution was stripped of solvent and the residual yellow syrup was purified by flash chromatography (3.5×25 cm silica) using a gradient of ethyl acetate in hexanes (10% triethylamine). The product eluted with 1:8:1 ethyl acetate-hexanes-triethylamine. Removal of solvents gave 667 mg (65% yield) of the phosphoramidite (2) as a pale yellow syrup: TLC (1:8:1 ethyl acetate-hexanes-triethylamine) $R_f$=0.32, spot stained orange upon spraying with 10% sulfuric acid in methanol.

EXAMPLE VII

Synthesis of Polyethylene Glycol Phosphoramidites ((2-Cyanoethoxy)-N,N'-diisopropylamino-13-[1-O-(4,4'-dimethoxytrityl)-1,4,7,10,13-pentaoxatridecyl]phosphine (3)). The alcohol precursor to the phosphoramidite (3) was first prepared. After drying by coevaporation with pyridine, 7.8 g (40 mmol) of tetraethyleneglycol (Pfaltz & Bauer) in 45 mL of dry pyridine was treated with 4.42 g (13 mmol) of dimethoxytrityl chloride for 1 hr at RT under argon. The mixture was evaporated in vacuo and purified by flash chromatography on RP column (5×30 cm, BAKERBOND Octadecyl $C_{18}$), 40 μm Prep LC Packing) using 90% (v/v) methanol with 0.02% triethylamine as the eluent. Removal of solvents gave 3.75 g (58% yield) of the precursor to 3 as an oil: TLC (20:1 chloroform-ethanol) $R_f$=0.35, spot stained orange upon spraying with 10% sulfuric acid in methanol.

A fraction of the alcohol precursor (2.98 g, 6.0 mmol) was evaporated with dry pyridine (2×10 mL) and thoroughly dried in vacuo. The resulting oil was transferred to an argon atmosphere while still under vacuum and dissolved in a mixture of anhydrous N,N-diisopropylethylamine (4.3 mL, 24.7 mmol) and dichloromethane (135 mL). While swirling vigorously under argon, 2-cyanoethoxy-N,N'-diisopropylaminochlorophosphine (2.2 mL, 11.2 mmol) was added to the mixture dropwise for 1 min by syringe. The resulting solution was stirred for 1.5 hr and monitored by TLC (5:5:1 hexanes-dichloromethane-triethylamine). The resulting mixture (major spot of phosphoramidite with $R_f$ 0.64) was quenched with methanol (5 mL) and poured into 700 mL of 25:1 ethylacetate-triethylamine. The organic layer was washed with 10% sodium bicarbonate solution (2×300 mL) and saturated sodium chloride solution (2×300 mL). The organic layer was dried with sodium sulfate, filtered and the solvent was removed in vacuo. The product was purified by flash chromatography (4×30 cm silica). After washing with 200 mL of 5:5:1 hexanes-dichloromethane-triethylamine, phosphoramidite (3) was eluted with the same solvent mixture. Evaporation of the solvent gave 2.8 g (67% yield) of 3 as an oil: TLC (5:5:1 hexanes-dichloromethane-triethylamine) $R_f$=0.64, spot stained orange upon spraying with 10% sulfuric acid in methanol.

EXAMPLE VIII

Synthesis of Cyanuric Chloride Activated ODNs (CC-ODN4). To 5 mg (0.8 μmoles) of 5'-hexylamine modified oligonucleotide, ODN3 (0.494 mL of a 10.12 mg/mL solution) was added 3.2 mL of 0.1M sodium borate buffer (pH 8.3), 2.0 mL of 1.0M sodium borate buffer (pH 8.3), and 2.3 mL of water. To the stirred solution was added 0.8 mL (40 mg, 217 μmoles) of a 50 mg/mL stock solution of cyanuric chloride in acetonitrile. After 40 min, the excess cyanuric chloride was removed by ultrafiltration through a 3000 MW cutoff membrane (Amicon, Beverly, Mass.) using 0.1M sodium borate buffer (pH 8.3, 3×10 mL) as the wash solution. After the final wash, the retentate was brought to a final volume of 15.0 mL with 0.1M borate buffer. The yield of CC-ODN4 was determined by $A_{260}$ to be 3.91 mg (79% recovery). C18 HPLC analysis indicated complete conversion of ODN3 (8.8 min peak) to CC-ODN4 (11.6 min peak) and no detectable cyanuric chloride (7.0 min). The product was used immediately for further reaction (EXAMPLE VI).

EXAMPLE IX

Synthesis of ODN-Polyethyleneimine Conjugates (ODN4-10K PEI). To a freshly prepared solution of 3.91 mg (0.636 μmoles) of CC-ODN4 in 15 mL of 0.1M sodium borate buffer (pH 8.3), was added 3.91 mL of 5M NaCl and an additional 0.64 mL of 0.1M sodium borate buffer. The mixture was vortexed in a 50 mL polypropylene tube. A 5.5 mg/mL stock solution of purified 10,000 MW PEI in 0.1M borate buffer was prepared. 231 μL of the PEI solution (1.27 mg, 0.127 μmoles) was added in 10 μL aliquots to the stirred solution of CC-ODN3. The tube was heated at 50° C. for 12 h. 235 μL (23.5 mg) of a 100 mg/mL solution of succinic anhydride in 1-methyl-2-pyrrolidinone was added to the ODN-PEI conjugate. The solution was vortexed and then gently rocked for 45 min. The heterogeneous mixture was centrifuged at 1500 g to remove solids. The supernatant was purified by ultrafiltration through a 30,000 MW cutoff membrane (Diaflo) using 10 mM Tris (pH 7.5, 3×10 mL) as the wash solution. After the final wash, the retentate was brought to a final volume of 3.5 mL with pH 7.5 Tris. The yield of recovered ODN3-conjugate was determined by $A_{260}$ to be 3.52 mg (90% recovery). Based on the stoichiometry, the average ratio of ODN4:10K PEI is ~5:1. Gel filtration HPLC analysis (Zorbax, GF-250 column) indicated complete conversion of CC-ODN4 (10–11 min peak) to ODN4-PEI (7.9 min peak).

EXAMPLE X

Synthesis of Carbohydrate Containing CAP Reagents (Tetrafluorophenyl 3-(2,3,4,6-tetra-O-acetyl-1-thio-β-D-galactopyranosyl)propionate (4a)). Tetra-O-acetyl-D-galactosyl bromide (Sigma) was converted to the thiopseudourea (TPU) derivative by treatment with thiourea in acetone according to the literature procedure (Stowell, C. P., and Lee, Y. C. (1982) Preparation of neoglycoproteins using 2-imino-2-methoxyethyl 1-thioglycosides. Methods in Enzymology, 83, 278). This TPU derivative was reacted with 3-iodopropionic acid (Aldrich) according to the literature procedure (Ponpimom, M. M., et al (1981) Cell-Specific Ligands For Selective Drug Delivery To Tissues And Organs, *J. Med. Chem.*, 24, 1388) to give 2-carboxyethyl 2,3,4,6-tetra-O-acetyl-1-thio-β-D-galactopyranoside. The crude material was purified by flash chromatography (3.5× 30 cm silica) using a gradient of methanol in methylene chloride. The product eluted with 10% methanol. Removal of solvent gave 135 mg (20% yield) of the carboxylic acid as a yellow syrup. The tetrafluorophenyl ester (4a) was prepared from 0.13 g (0.35 mmol) of the carboxylic acid by treatment with 1.5 equivalents of tetrafluorophenyl trifluoroacetate in $CH_2Cl_2$ in the presence 2 equivalents of triethylamine.

HPLC using a 250×10 mm C-18 column (flow rate=4.7 mL/min). The pure fraction was concentrated to give 1.46 mg of ODN3-PEP4 (60% recovery).

A solution of 1.46 mg (0.262 μmoles) of ODN3-PEP4 in 0.50 mL of water was combined with 0.25 mL of 1.0M borate buffer (pH 8.3). Iodoacetic anhydride was added as a 50 mg/mL stock solution in acetonitrile (185 μL, 9.2 mg, 26 μmoles). HPLC analysis after 2 hours showed reaction of ODN3-PEP4 to IA-ODN3-PEP4 (15.0 min). The mixture was purified by ultrafiltration as described in EXAMPLE I. The yield of purified IA-ODN3 was 0.72 mg (48% recovery). The synthetic results are presented in Table 1.

TABLE I

Properties of Modified Oligonucleotides (ODNs)

| ODN[a] | 5'-mod | 3'-mod | MW | $A_{260} = 1$[b] (μg/mL) | HPLC[c] min | yield[d] % |
|---|---|---|---|---|---|---|
| ODN1 | hexylamine | none | 4931 | 35.4 | 8.4 | — |
| ODN2 | hexylamine | hexanol | 7666 | 33.0 | 9.8 | — |
| ODN3 | hexylamine | hexanol | 4893 | 35.7 | 9.5 | — |
| ODN4 | hexylamine | none | 6264 | 35.2 | 8.8 | — |
| IA-ODN1 | iodoacetamide | none | 5140 | 31.9 | 9.2 | 76[e] |
| IA-ODN2 | iodoacetamide | hexanol | 7834 | 33.7 | 10.7 | 82 |
| IA-ODN3 | iodoacetamide | hexanol | 5061 | 36.9 | 10.9 | 77 |
| CC-ODN4 | cyanuric chloride | none | 6412 | 36.0 | 11.6 | 79 |
| ODN1-PEP1 | PEP1 | none | 6210 | 38.6 | 9.0 | 30[e] |
| ODN1-PEP2 | PEP2 | none | 6435 | 39.9 | 13.0 | 73 |
| ODN1-PEP3 | PEP3 | none | 6652 | 41.3 | 15.4 | 67 |
| ODN2-PEP1 | PEP1 | hexanol | 8904 | 38.3 | 10.0 | 98 |
| ODN2-PEP2 | PEP2 | hexanol | 9129 | 39.3 | 13.4 | 97 |
| ODN2-PEP3 | PEP3 | hexanol | 9346 | 40.2 | 15.6 | 87 |
| ODN3-PEP4 | PEP4 | hexanol | 5550 | 40.5 | 12.0 | 60 |
| IA-ODN3-PEP4 | IA-PEP4 | hexanol | 5718 | 41.7 | 15.0 | 48 |

[a]The sequences of the oligonucleotides and peptides are as described in the SPECIFIC EXAMPLES.
[b]Calculated concentration of ODN that gives 1.00 absorbence units at 260 nm.
[c]Elution time; C-18 EPLC system described in FIG. 5.
[d]% Isolated yield of ODN after purification as described in EXAMPLES.
[e]Purified by PRP-1 HPLC using the gradient described in FIG. 5 (flow rate = 2 mL/min).

Tetrafluorophenyl trifluoroacetate (TFP-TFA) was prepared from 2,3,5,6-tetrafluorophenol by refluxing with trifluoroacetic anhydride, neat. TFP-TFA was isolated by distillation (b.p. 62° C./18 mm).

The product 4a was purified by flash chromatography (1×37 cm silica) using a gradient of ethyl acetate in hexane. The product eluted with 20% ethyl acetate. Removal of solvent gave 125 mg (67% yield) of 4a as a pale yellow syrup: TLC (1:2 ethyl acetate-hexanes) $R_f$=0.30, stained black upon charring with 10% sulfuric acid in methanol.

EXAMPLE XI

Synthesis of Iodoacetamide Derivative of ODN-Peptide Conjugate (IA-ODN3-PEP4).

A solution of 3.0 mg (0.613 μmoles) of ODN3 in 0.39 mL of 0.1M borate buffer (pH 8.3) was treated with iodoacetic anhydride and purified by ultrafiltration as described in EXAMPLE I. The yield of purified IA-ODN3 solution was 2.4 mg (77% recovery).

A solution of 2.2 mg (0.435 μmoles) IA-ODN3 solution in 1.00 mL of 0.1M borate buffer was treated with a solution of 1.34 mg (2.12 μmoles) of PEP4 in degassed water as described in EXAMPLE II. HPLC analysis after 1.5 hours showed complete conversion of IA-ODN3 (10.9 min) to ODN3-PEP4 (12.0 min). ODN3-PEP4 was purified by

What is claimed is:

1. An oligonucleotide-peptide-carrier conjugate wherein the oligonucleotide, peptide and carrier moieties are covalently linked to one another, and wherein:

the oligonucleotide is selected from a group consisting of antisense oligonucleotide, antigene oligonucleotide, protein binding oligonucleotide and ribozyme which selectively binds to a desired sequence of RNA, DNA or protein in a target cell, and which by binding to the desired RNA, DNA or protein sequence brings about a desired therapeutic effect, the oligonucleotide optionally being modified relative to naturally occurring oligonucleotides to increase binding to the desired RNA, DNA or protein sequence or to increase resistance to nuclease enzymes;

the peptide is cleavable by protease enzymes within the lysosomes of a target cell, and the carrier is a lysosomotropic carrier which is capable of facilitating transport of the oligonucleotide-peptide-carrier conjugate into the target cell.

2. The oligonucleotide-peptide-carrier conjugate of claim 1 wherein the oligonucleotide is an antisense oligonucleotide.

3. The oligonucleotide-peptide-carrier conjugate of claim 1 wherein the oligonucleotide is an antigene oligonucleotide.

4. The oligonucleotide-peptide-carrier conjugate of claim 1 wherein the oligonucleotide is a protein binding oligonucleotide.

5. The oligonucleotide-peptide-carrier conjugate of claim 1 wherein the oligonucleotide is a ribozyme.

6. The oligonucleotide-peptide-carrier conjugate of claim 1 wherein the peptide includes the sequence selected from the group consisting of -leu-ala-leu-ala- (Sequence ID No.: 13), gly-phe-leu-gly- (Sequence ID No.: 2) and gly-phe-tyr-ala (Sequence ID No.: 12).

7. The oligonucleotide-peptide-carrier conjugate of claim 1 wherein the peptide includes the sequence selected from the group consisting of $H_2N$-cys-leu-ala-leu-ala-lys-$CONH_2$ (Sequence ID No.: 6), $H_2N$-cys-gly-phe-leu-gly-lys-$CONH_2$ (Sequence ID No.: 7) and $N_2N$-cys-gly-phe-tyr-ala-lys-$CONH_2$ (Sequence ID No.: 15).

8. The oligonucleotide-peptide-carrier conjugate of claim 1 wherein the carrier is a lipophilic group.

9. The oligonucleotide-peptide-carrier conjugate of claim 1 wherein the peptide is covalently linked to the 5' or 3' tail of the ODN through a covalent linkage which comprises the structure ODN-5' or 3'-O—P(O,O⁻)—O(CH$_2$)$_o$—NH—CO—CH$_2$—S-PEPTIDE-NH— where o is an integer beween 2 and 12, ODN represents the oligonucleotide and PEPTIDE represents the residue of the peptide moiety.

10. The oligonucleotide-peptide-carrier conjugate of claim 9 wherein o is 6.

11. The oligonucleotide-peptide-carrier conjugate of claim 1 wherein the peptide is covalently linked to the carrier moiety through a covalent linkage which comprises the structure

-PEPTIDE-NH—CO—CH$_2$—S-CARRIER, wherein PEPTIDE represents the residue of the peptide, and CARRIER represents residue of the carrier moiety.

12. The oligonucleotide-peptide-carrier conjugate of claim 1 wherein the peptide is covalently linked to the 5' or the 3' tail of the ODN through a covalent linkage which comprises the structure ODN-5' or 3'-O—P(O,O⁻)—O(CH$_2$)$_o$—NH—CO—CH$_2$—S-PEPTIDE -NH— and wherein the peptide is covalently linked to the carrier moiety through a covalent linkage which comprises the structure -PEPTIDE-NH—CO—CH$_2$—S-CARRIER, or -PEPTIDE-NH—W—NH-CARRIER where o is an integer beween 2 and 12, ODN represents the oligonucleotide moiety, PEPTIDE represents the residue of the peptide moiety, CARRIER represents residue of the carrier moiety and W represents an chlorinated symmetrical triazine moiety which is obtained when a nucleophilic NH$_2$ group of the peptide moiety and a nucleophilic NH$_2$ group of the carrier moiety is bridged by reaction with cyanuric chloride.

* * * * *

UNITED STATES PATENT AND TRADEMARK OFFICE
CERTIFICATE OF CORRECTION

PATENT NO. : 5,574,142
DATED : November 12, 1996
INVENTOR(S) : Meyer, Jr. et al.

It is certified that error appears in the above-indentified patent and that said Letters Patent is hereby corrected as shown below:

Column 1, line 64, "phophoramidates" should be --phosphoramidates--;

Column 10, line 16, "C18" should be --C-18--;

Column 13, line 6, "$PO_2$-O-" should be -- $PO^-_2$-O- --;

Column 22, line 15, before GTTCTCCAT-" add --5'--;

Column 22, line 44, "28@C" should be --28°C--;

Column 23, line 44, "C18" should be --C-18--;

Column 23, line 59, "C18" should be --C-18--;

Column 26, line 23, "C18" should be --C-18--;

Column 38, line 48, "an" should be --a--.

UNITED STATES PATENT AND TRADEMARK OFFICE
CERTIFICATE OF CORRECTION

PATENT NO. : 5,574,142
DATED : November 12, 1996
INVENTOR(S) : Meyer, Jr. et al.

It is certified that error appears in the above-indentified patent and that said Letters Patent is hereby corrected as shown below:

Column 11, line 15, "Tm" should be --$T_m$--;

Column 23, line 20, "$^{18}$0.1mL" should be --$\sim$0.1mL--;

Column 23, line 30, after "decomposition" please insert

--The HPLC system used a 250 x 4.6 mm C-18 column and a gradient of 5-45% solvent B over 20 min. (flow rate = 1 mL/min) where solvent A = 0.1 M triethylammonium acetate (pH7.5), solvent B=acetonitrile; detection was by UV absorbance at 260 nm. Panel A: Starting hexylamine modified ODN (ODN2). Panel B: Reaction of ODN2 (IA-ODN2) with iodoacetic anhydride at 60 min. Panel C: Iodoacetamide modified ODN (IA-ODN2) after purification by ultrafiltration. Panel D: ODN2-PEP2 after purification by C-18 HPLC. --;

Column 24, line 37, after "lanes 1-6)' please insert

--PAGE was carried out with denaturing cross-linked 20% gels (bisacrylamide / acrylamide, 1:19; 0.4 x 170 x 390 mm) at 45 watts for 40 min. Nucleosidic bands were visualized by staining with methylene blue (0.02%). Bromophenol blue was used as a marker. Lane 1 is ODN1-PEP1. Lane 2 is ODN1-PEP1 after trypsin. Lane 3 is ODN-PEP2. ~~Lane 4~~ is ODN1-PEP2 after trypsin. Lane 5 is ODN1-PEP3. Lane 6 is ODN1-PEP3 after trypsin. Lane 7 is IA-ODN1. Lane 8 is ODN1. Lane 9 is ODN1 after trypsin.--;

UNITED STATES PATENT AND TRADEMARK OFFICE
CERTIFICATE OF CORRECTION

PATENT NO. : 5,574,142
DATED : November 12, 1996
INVENTOR(S) : Meyer, Jr. et al.

It is certified that error appears in the above-indentified patent and that said Letters Patent is hereby corrected as shown below:

Column 28, Table I, the last column, "73" should be --$73^e$-- and "67" should be --$67^e$--;

Column 28, line 3 (Footnotes of Table 1.) "EPLC" should be --HPLC--.

Signed and Sealed this

Fifteenth Day of April, 1997

Attest:

BRUCE LEHMAN

Attesting Officer   Commissioner of Patents and Trademarks

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:1:

Ala  Leu  Ala  Leu
   1

( 2 ) INFORMATION FOR SEQ ID NO:2:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:2:

Gly  Phe  Leu  Gly
   1

( 2 ) INFORMATION FOR SEQ ID NO:3:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
      ( A ) ORGANISM: Simian Virus 40

( x i ) SEQUENCE DESCRIPTION: SEQ ID NO:3:

Cys  Thr  Pro  Pro  Lys  Lys  Lys  Arg  Lys  Val
   1                   5                        10

( 2 ) INFORMATION FOR SEQ ID NO:4:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide (iii) HYPOTHETICAL: NO (v) FRAGMENT TYPE: C-terminal (vi) ORIGINAL SOURCE:
    (A) ORGANISM: Influenza virus (xi) SEQUENCE DESCRIPTION: SEQ ID NO:4:

```
Cys  Asn  Ser  Ala  Ala  Phe  Glu  Asp  Leu  Arg  Val  Leu  Ser
1                  5                        10
```

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: yeast (xi) SEQUENCE DESCRIPTION: SEQ ID NO:5:

```
Met  Asn  Lys  Ile  Pro  Ile  Lys  Asp  Leu  Leu  Asn  Pro  Gln  Cys
1                  5                        10
```

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Cys  Leu  Ala  Leu  Ala  Lys
1                  5
```

(2) INFORMATION FOR SEQ ID NO:7:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:7:

```
Cys  Gly  Phe  Leu  Gly  Lys
1                  5
```

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (iii) HYPOTHETICAL: NO ( i v ) ANTI-SENSE: YES ( v i ) ORIGINAL SOURCE:
    ( A ) ORGANISM: Hepatitis B virus ( i x ) FEATURE:
    ( A ) NAME/KEY: modified_base
    ( B ) LOCATION: 1
    ( D ) OTHER INFORMATION: /mod_base=OTHER
        / note="Nucleotide 1 is H2N-(CH2)6-OPO2-5'O-C."

( x i ) SEQUENCE DESCRIPTION: SEQ ID NO:8:

CTCCATCTTC GTCACA           16

( 2 ) INFORMATION FOR SEQ ID NO:9:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: YES ( v i ) ORIGINAL SOURCE:
    ( A ) ORGANISM: Paramecium tetraurelia ( i x ) FEATURE:
    ( A ) NAME/KEY: modified_base
    ( B ) LOCATION: 1
    ( D ) OTHER INFORMATION: /mod_base=OTHER
        / note="Nucleotide 1 is H2N-(CH2)6-OPO2-5'O-T"

( i x ) FEATURE:
    ( A ) NAME/KEY: modified_base
    ( B ) LOCATION: 27
    ( D ) OTHER INFORMATION: /mod_base=OTHER
        / note="Nucleotide 27 is T-O-PO2-3'O-(CH2)6-OH"

( x i ) SEQUENCE DESCRIPTION: SEQ ID NO:9:

TAATTATTCA GCCATTTATT ATTAGTT           27

( 2 ) INFORMATION FOR SEQ ID NO:10:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: YES ( v i ) ORIGINAL SOURCE:
    ( A ) ORGANISM: Hepatitis B virus ( i x ) FEATURE:
    ( A ) NAME/KEY: modified_base
    ( B ) LOCATION: 1
    ( D ) OTHER INFORMATION: /mod_base=OTHER
        / note="Nucleotide 1 is H2N-(CH2)6-OPO2-5'-O-G."

( x i ) SEQUENCE DESCRIPTION: SEQ ID NO:10:

GTTCTCCATG TTCAG           15

( 2 ) INFORMATION FOR SEQ ID NO:11:

( i ) SEQUENCE CHARACTERISTICS:
    ( A ) LENGTH: 20 base pairs
    ( B ) TYPE: nucleic acid (C) STRANDEDNESS: single
(D) TOPOLOGY: linear (iii) HYPOTHETICAL: NO (iv) ANTI-SENSE: NO (ix) FEATURE:
(A) NAME/KEY: modified_base
(B) LOCATION: 1
(D) OTHER INFORMATION: /mod_base=OTHER
/ note="Nucleotide 1 is H2N-(CH2)6-OPO2-5'-O-C."

(xi) SEQUENCE DESCRIPTION: SEQ ID NO:11:

CTGCTGCCTC CCGTAGGAGT                                                        20

(2) INFORMATION FOR SEQ ID NO:12:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:12:

Gly  Phe  Tyr  Ala
 1

(2) INFORMATION FOR SEQ ID NO:13:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (iii) HYPOTHETICAL: NO (xi) SEQUENCE DESCRIPTION: SEQ ID NO:13:

Leu  Ala  Leu  Ala
 1

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear (iii) HYPOTHETICAL: NO (xi) SEQUENCE DESCRIPTION: SEQ ID NO:14:

GTGACGAACA TGGAGAACAT                                                        20

(2) INFORMATION FOR SEQ ID NO:15:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (xi) SEQUENCE DESCRIPTION: SEQ ID NO:15:

```
Cys  Gly  Phe  Tyr  Ala  Lys
1                    5
```